United States Patent [19]

Kuo et al.

[11] Patent Number: 5,240,947
[45] Date of Patent: Aug. 31, 1993

[54] 2,3,4,5-SUBSTITUTED FURO[2,3-C]PYRAZOLE DERIVATIVES

[75] Inventors: Sheng-Chu Kuo; Li-Jiau Huang, both of Taichung; Che-Ming Teng, Taipei, all of Taiwan

[73] Assignee: National Science Council, Taipei, Taiwan

[21] Appl. No.: 985,798

[22] Filed: Nov. 30, 1992

[51] Int. Cl.$^5$ .................. A61K 31/41; A61K 31/415; C07D 491/048

[52] U.S. Cl. .................... 514/364; 514/403; 548/144; 548/360.5

[58] Field of Search ............. 548/144, 360.5; 514/364, 403

[56] References Cited

PUBLICATIONS

Azis et al, Chemical Abstracts, vol. 102 No. 78768a (1984).

Huang et al, Chemical Abstracts, vol. 93 No. 71631n (1979).

Sheng-Chu Kuo, et al., "Studies on Heterocyclic Compounds..." Journal of Medicinal Chemistry, 1984, vol. 27, No. 4, pp. 539-544.

Li-Jiau Huang, et al., "Synthesis and Antiplatelet Activities ...", 1992 Pharmaceutical Society of Japan, Sep. 1992, pp. 2547-2551, vol. 40, No.9.

Li-Jiau Huang, et al., "Studies on Heterocyclic Compounds ... ", Journal of the Taiwan Pharmaceutical Assoc., vol. 31, No. 1 (1979), pp. 48-56.

*Primary Examiner*—Robert W. Ramsuer
*Attorney, Agent, or Firm*—Winstead Sechrest & Minick

[57] ABSTRACT

The present invention provides a novel series of 2,3,4,5-substituted furo[2,3-c]pyrazole compounds. These compounds are found potent in inhibiting thrombocyte aggregation and antiallergy effect.

3 Claims, No Drawings

2,3,4,5-SUBSTITUTED FURO[2,3-C]PYRAZOLE DERIVATIVES

TECHNICAL FIELD OF THE INVENTION

The present invention relates to new and useful furo[2,3-c]pyrazole derivatives, especially relates to 2,3,4,5-substituted furo[2,3-c]pyrazole derivatives.

BACKGROUND OF THE INVENTION

Furo[2,3-c]pyrazole compounds were first synthesized by two of the present inventors, L. J. Haung and S. C. Kuo, and H. T. Li in an article published in *J. Taiwan Pharm. Assoc.* 31 (1), 47–55 (1979). Ethyl 3-methyl-1-phenylfuro[2,3-c]pyrazole-5-carboxylate (3) was synthesized in this article. As shown in the following Scheme 1, chloro-3-methyl-1-phenylpyrazole-4-carboxaldehyde (1) and ethylglycolate (2) were condensed to form ethyl 3-methyl-1-phenylfuro[2,3-c]pyrazole-5-carboxylate (3); or 5-hydroxy-3-methyl-1-phenyl-pyrazole-4-carboxal-dehyde acetate (4) was reacted with ethylbromoacetate (5) to obtain the ethyl 3-methyl-1-phenylfuro[2,3-c]pyrazole-5-carboxylate (3). The product produced by these two methods are very low in yield and stability. Therefore, only one furo[2,3-c]pyrazole compound (3) was synthesized and no further investigation was conducted in the above-mentioned article.

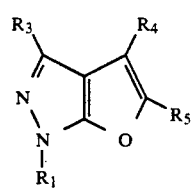
(A)

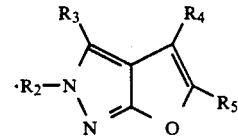
(B)

SUMMARY OF THE INVENTION

The present invention provide a novel series of 2,3,4,5-substituted furo[2,3-c]pyrazole compounds having the formula:

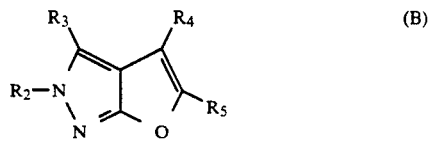
(B)

wherein $R_2$ represents $C_{1-11}$ alkyl; hydroxy $C_{1-4}$ alkyl;

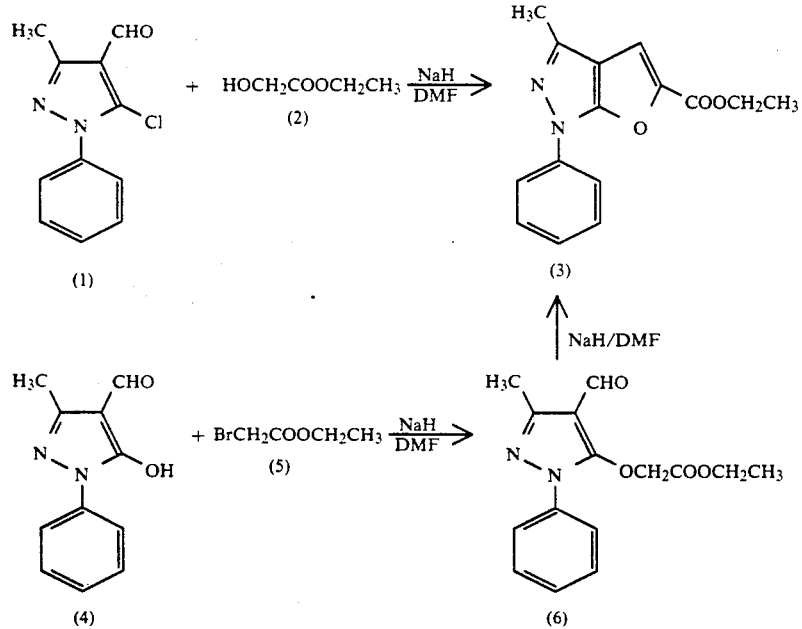

Scheme 1

The compound (3) as described above is in the class of $N^1$-substituted furo[2,3-c]pyrazole compounds having the formula (A). As to $N^2$-substituted furo[2,3-c]pyrazole compounds having the formula (B) have not yet been reported in any literatures.

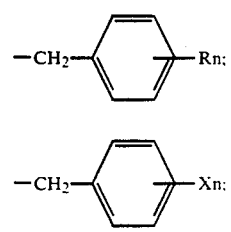

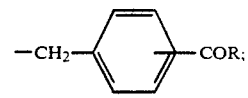

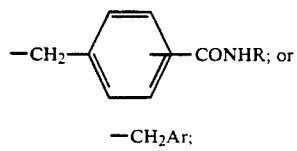

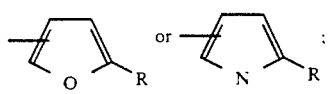

wherein Ar represents , , or ;

R is hydrogen or $C_{1-6}$ alkyl; n=1 or 2, and X is halogen;
$R_3$ represents $C_{1-9}$ alkyl;
$R_4$ represents $C_{1-9}$ alkyl;
$R_5$ represents hydrogen; —COR; —CH$_2$OH; —CH$_2$OCOR$_1$;
—COX;
—COOR;
—CONHR$_a$;
—CONR$_1$R$_1$;

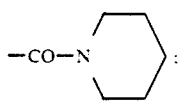

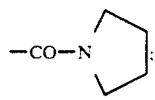

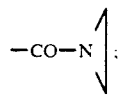

—CONHAr$_1$;

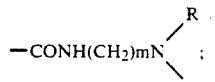

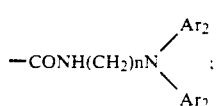

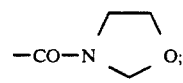

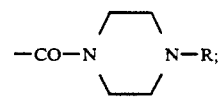

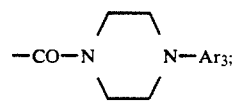

—CONH(CH$_2$)nAr$_3$n;
—CH=CHCONHR;
—CH=CH—COOR;
—CH=C(COOR)$_2$;
—CONHNHCOOR; or

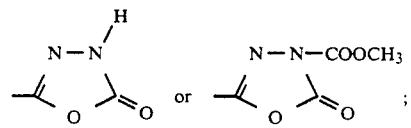

wherein Ar$_1$ is 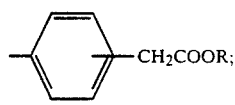

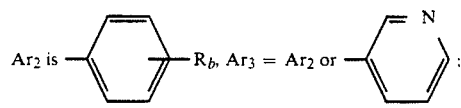

m=1-3; R$_1$ is $C_{1-6}$ alkyl, R$_a$ is R or $C_{3-6}$ cycloalkyl; R$_b$ is hydrogen, halogen or —OCH$_3$; and
R, n and X have the same meanings as defined above; or
pharmaceutically acceptable salts thereof.

The compounds represented by formula (B) include racemic mixture of optically active compounds and optically pure R and S steroisomers.

The compounds of formula (B) are excellent in thrombocyte aggregation inhibiting activity and antiallergic activity and are, therefore, useful as pharmaceuticals. Moreover, the compounds of formula (B) are relatively easier to be synthesized and can be synthesized in industrially acceptable yields.

Scheme 2

Part one: preparation of 2,3,4-Trisbubstituted furo[2,3-c]pyrazole-5-carboxylic acid (III)

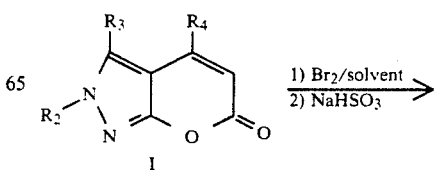

-continued
Scheme 2

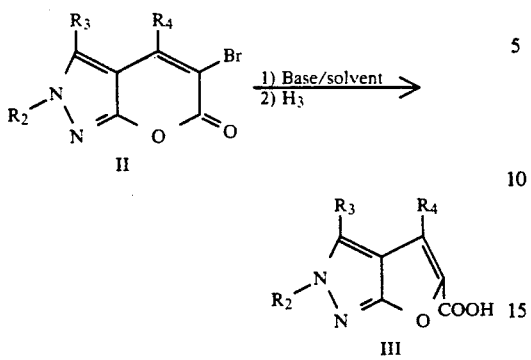

wherein R₂, R₃ and R₄ have the same meanings as defined above.

The starting material 2,3,4-trisubstituted pyrano[2,3-c]-pyrazol-6-ones (I) used in the scheme 2 reaction can be prepared according to the method reported by two of the present inventors, S. C. Kuo and L. J. Huang, and H. Nakamura in *J. Med. Chem.*, 27 (4), 539–544 (1984) or the method reported by L. J. Haung et al. in *Pharm. Society of Japan*, 40 (9), 2547–2551 (1992), details thereof are incorporated by reference. The method of preparation of compound I comprises reacting hydrazine with an excess amount of acyl acetate to form 3,4-disubstituted pyrano[2,3-C]pyrazol-6-ones, reacting the resulting 3,4-disubstituted pyrano[2,3-C]pyrazol-6-ones with an alkyl halide to give 2,3,4-trisubstituted pyrano[2,3-c]pyrazol-6-one (I).

The compound I, as shown in scheme 2, was dissolved in an suitable organic solvent, e.g. chloroform, and then Br₂ (molar ratio of Br₂ to compound I=1:1) was added to carry out bromination, followed by NaHSO₃ treatment to remove one molecule of HBr such that trisubstituted-5-bromo-pyrano[2,3-c]pyrazol-6-one (II) was formed.

The compound II was dissolved in a suitable solvent medium, e.g. n-butanol, and the solution was heated until it boils, and then a strong base was gradually added to react with the compound II. The completion of the reaction can be detected by thin layer chromatography. When the reaction was completed, the solvent was removed by vaporization, and the remaining reaction mixture was washed with water. The aqueous layer was acidified to obtain 2,3,4-trisubstituted furo[2,3-c]pyrazole-5-carboxylic acid (III) as a precipitate, which can be purified by column chromatography or recrystalization.

EXAMPLE 1-1

5-bromo-2,3,4-trimethylpyrano[2,3-c]pyrazol-6-(1H)-one (II-1)

To a solution of 2,3,4-trimethylpyrano[2,3-c]pyrazol-6(1H)-one (I-1) (5 g, 0.028 mol) in 75 ml of chloroform, a bromine-chloroform solution which was prepared by dissolving bromine (4.5 g, 0.028 mol) in 50 ml chloroform was added dropwise at room temperature. After the reaction was completed, sodium bisulfite was added until the color of the reaction mixture turn to light yellow. The reaction mixture was then filtered, and the filtrate was washed with water and dried with anhydrous magnesium sulfate, and it was then filtered again. After the solvent medium was removed by evaporation, white crystalline powder was obtained as residue, which was recrystallized from chloroform-ethanol (1:3) to give compound II-1 i the form of white needle crystal. Yield, 6.5 g (90%).

mp: 203°–206° C.; IR(KBr) $v_{max}$: 1720(C=O)cm$^{-1}$; UV (CHCl₃) $\lambda_{max}$: 314.5 nm; ¹H-NMR(CDCl₃) δ:2.33(s,3H, C-4-CH₃), 2.36(s,3H,C-3-CH₃), 3.83(s,3H,N-CH₃); MS, m/z: 257(M+). Anal. calcd for C₉H₉BrN₂O₂: C, 42.05; H, 3.53; N, 10.90. Found: C, 42.11; H, 3.50; N, 10.95.

2,3,4-trimethylfuro[2,3-c]pyrazole-5-carboxylic acid (III-1)

Method I

Metal sodium (0.2 g, 0.0087 mol) was dissolved in 200 ml of ethanol to get sodium ethoxide solution. Compound II-1 (0.5 g, 0.002 mol) was suspended in 250 ml of ethanol, and the sodium ethoxide solution was added dropwise under heating with reflux. The stirring was maintained until the reaction was completed. 10 ml of water was added to the reaction mixture, which was then heated under reflux for 10 min, and the solvent thereof was distilled off. The residue was washed with water, and the aqueous layer was acidified with 10% HCl solution. The precipitate formed by acidification was collected by filtration and was recrystalized from ethanol to get compound III-1 in the form of yellow brown crystal. Yield, 0.06 g (15%).

mp: 206°–208° C.; IR(KBr) $v_{max}$: 3050 (COOH)cm$^{-1}$, 1670 (C=O)cm$^{-1}$; UV(CHCl₃) $\lambda_{max}$: 280 nm; ¹H-NMR(DMSO-d₆) δ:2.43(s,6H,C-3—CH₃ and C-4—CH₃), 3.76(s,3H,N-CH₃); MS, m/z: 194(M+). Anal. Calcd for C₉H₁₀N₂O₃: C, 55.67; H, 5.19; N, 14.43. Found: C, 55.70; H, 5.22; N, 14.50.

Method II

Metalic sodium (0.2 g, 0.0087 mol) was dissolved in 100 ml of ethanol and the solvent was distilled off, and then 50 ml of benzene and 7 drops of crown ether were added and mixed fully. To the mixture a solution of compound II-1 (1.0 g, 0.004 mol) in 300 ml of benzene at 70° C. was added dropwise and slowly, which was then heated with reflux for one hour. 100 ml of water was added to the heated mixture, which was heated with reflux for 10 min. The reaction mixture was extracted with water and the extract was acidified with 10% HCl solution. The precipitate formed by acidification was collected by filtration and recrystalized from ethanol to give compound III-1 in the form of yellow brown needle crystal. Yield, 0.42 g (55%). mp: 206°–208° C.

IR of the product obtained by method II was compared with that of compound III-1 obtained by method I, and a mixed melting point test was conducted. The results show the compounds obtained by these two methods are the same compound.

Method III

Metalic sodium (2 g, 0087 mol) was dissolved in 200 ml of n-butanol to get sodium butoxide. Compound II-1 (5 g, 0.02 mol) was dissolved in 250 ml of n-butanol and the temperature of mixture was raised to 120° C., followed by adding the butoxide solution prepared above dropwise and slowly to the heated mixture while stirring. After the reaction was completed, 100 ml of water was added and heated with reflux for 10 min, and then the reaction mixture was washed with water. The aqueous layer was acidified with 10% HCl solution (pH=1)

and a precipitate was formed. The precipitate was collected by filtration and recrystalized from ethanol to give compound III-1 in the form of yellow brown needle crystal. Yield, 2.32 g (65%). mp: 206°-208° C.

IR of the product obtained by method III was compared with that of compound III-1 obtained by methods I and II, and a mixed melting point test was conducted. The results show the compounds obtained by method III are same as the compounds obtained by methods I and II.

EXAMPLE 1-2

5-bromo-2-ethyl-3,4-dimethylpyrano[2,3-c]pyrazol-6(2H)-one (II-2)

To a solution of 2-ethyl-3,4-dimethylpyrano[2,3-c]pyrazol-6(2H)-one (I-2) (5 g, 0.026 mol) in 75 ml of chloroform, a bromine-chloroform solution which was prepared by dissolving bromine (4.5 g, 0.028 mol) in 50 ml chloroform was added dropwise at room temperature. After the reaction was completed, sodium bisulfite was added until the color of the reaction mixture turn to light yellow. The reaction mixture was then filtered, and the filtrate was washed with water several times and dried with anhydrous magnesium sulfate, and it was then filtered again. After the solvent medium was removed by evaporation, the residue was recrystalized from chloroform-ethanol to give compound II-2 in the form of white needle crystal. Yield, 6.5 g (85%).

mp: 135°-137° C.; IR(KBr) $\nu_{max}$: 1720(C=O)cm$^{-1}$; UV (CHCl$_3$) $\lambda_{max}$: 315.5 nm; $^1$H-NMR(CDCl$_3$) $\delta$:1.37(t,3H,-CH$_2$CH$_3$), 2.23(s,3H,C-4-CH$_3$), 2.43(s,3H,C-3—CH$_3$), 4.07(q,2H,-CH$_2$CH$_3$); MS, m/z: 271(M$^+$). Anal. Calcd for C$_{10}$H$_{11}$BrN$_2$O$_2$: C, 44.30; H, 4.09; N, 10.33. Found: C, 44.20; H, 4.00; N, 10.31.

2-ethyl-3,4-dimethylfuro[2,3-c]pyrazole-5-carboxylic acid (III-2)

Metalic sodium (2 g, 0087 mol) was dissolved in 200 ml of n-butanol to get sodium butoxide. Compound II-2 (5 g, 0.018 mol) was dissolved in 250 ml of n-butanol and the temperature of mixture was raised to 120° C., followed by adding the butoxide solution prepared above dropwise and slowly to the heated mixture while stirring. After the reaction was completed, 100 ml of water was added and heated with reflux for 10 min, and then the reaction mixture was washed with water. The aqueous layer was acidified with 10% HCl solution (pH=1) and a precipitate was formed. The precipitate was collected by filtration and recrystalized from ethanol to give compound III-2 in the form of light yellow needle crystal. Yield, 3.2 g (85%).

mp: 203°-205° C.; IR(KBr) $\nu_{max}$: 2500-3300(—OH)cm$^{-1}$, 1690(C=O)cm$^{-1}$; UV(C$_2$H$_5$OH) $\lambda_{max}$: 285 nm; $^1$H-NMR(DMSO-d$_6$) $\delta$:1.33(t,3H,-CH$_2$CH$_3$), 2.47(s,6H,C-3—CH$_3$ and C-4—CH$_3$), 4.13(q,2H,—CH$_2$CH$_3$); MS, m/z: 208(M$^+$). Anal. Calcd for C$_{10}$H$_{12}$N$_2$O$_3$: C, 57.69; H, 5.81; N, 13.45. Found: C, 57.72; H, 5.63; N, 13.39.

EXAMPLE 1-3

5-bromo-2-isopropyl-3,4-dimethylpyrano[2,3-c]pyrazol-6(2H)-one (II-3)

The synthesis and purification procedures for preparing compound II-1 as described in Example 1-1 were repeated to obtain compound II-3 except that 2-isopropyl-3,4-dimethylpyrano[2,3-c]pyrazol-6(2H)-one (I-3) (5 g, 0.024 mol) was used instead of compound I-1. Compound II-3 obtained is in the form of white needle crystal. Yield, 6.5 g (85%).

mp: 164°-166° C.; IR(KBr) $\nu_{max}$: 1720(C=O)cm$^{-1}$; UV(CHCl$_3$) $\lambda_{max}$: 316 nm($\epsilon$=3.7×10$^4$); $^1$H-NMR(CDCl$_3$) $\delta$:1.33(d,6H,—CH(CH$_3$)$_2$, 2.43(s,3H,C-4—CH$_3$), 2.50(s,3H,C-3—CH$_3$), 5.43(s,1H,—CH—); MS, m/z: 284(M$^+$). Anal. Calcd for C$_{11}$H$_{13}$BrN$_2$O$_2$: C, 46.34; H, 4.60; N, 9.82. Found: C, 46.30; H, 4.66; N, 9.73.

2-isopropyl-3,4-dimethylfuro[2,3-c]pyrazole-5-carboxylicacid (III-3)

The synthesis and purification procedures for preparing compound III-1 as described in Example 1-1 were repeated to obtain compound III-3 except that compound II-3 (5 g, 0.018 mol) was used instead of compound II-1. Compound III-3 obtained is in the form of white crystal. Yield, 6.2 g (56%).

mp: 185°-187° C.; IR(KBr) $\nu_{max}$: 2250-3300(—OH)cm$^{-1}$, 1720(C=O)cm$^{-1}$; UV(C$_2$H$_5$OH) $\lambda_{max}$: 286.5 nm($\epsilon$=4.2×10$^4$); $^1$H-NMR(DMSO-d$_6$) $\delta$:1.33(d,6H,—CH(CH$_3$)$_2$), 2.48(s,6H,C-3—CH$_3$ and C-4—CH$_3$), 4.52(m,1H,—CH—); MS, m/z: 222(M$^+$). Anal. Calcd for C$_{11}$H$_{14}$N$_2$O$_3$: C, 59.45; H, 6.35; N, 12.60. Found: C, 59.40; H, 6.38; N, 12.73.

EXAMPLE 1-4

5-bromo-2-propyl-3,4-dimethylpyrano[2,3-c]pyrazol-6(2H)-one (II-4)

The synthesis and purification procedures for preparing compound II-1 as described in Example 1-1 were repeated to obtain compound II-4 except that 2-propyl-3,4-dimethylpyrano[2,3-c]pyrazol-6(2H)-one (I-4) (5 g, 0.024 mol) was used instead of compound I-1. Compound II-4 obtained is in the form of white crystal. Yield, 5.5 g (81%).

mp: 108°-110° C.; IR(KBr) $\nu_{max}$: 1720(C=O)cm$^{-1}$; UV(CHCl$_3$) $\lambda_{max}$: 302 nm($\epsilon$=8.4×10$^4$); $^1$H-NMR(CDCl$_3$) $\delta$:1.33(t,3H,—CH$_2$CH$_2$CH$_3$), 2.41(s,3H,C-4—CH$_3$), 2.36(s,3H,C-3—CH$_3$), 4.52(m,4H,—CH$_2$CH$_2$—); MS, m/z: 284(M$^+$). Anal. Calcd for C$_{11}$H$_{13}$BrN$_2$O$_2$: C, 46.34; H, 4.60; N, 9.82. Found: C, 46.39; H, 4.67; N, 9.70.

2-propyl-3,4-dimethylfuro[2,3-c]pyrazole-5-carboxylic acid (III-4)

The synthesis and purification procedures for preparing compound III-1 as described in Example 1-1 were repeated to obtain compound III-4 except that compound II-4 (5 g, 0.015 mol) was used instead of compound II-1. Compound III-4 obtained is in the form of white crystal. Yield, 1.7 g (30%).

mp: 180°-182° C.; IR(KBr) $\nu_{max}$: 2500-3300(—OH)cm$^{-1}$, 1720(C=O)cm$^{-1}$; UV(C$_2$H$_5$OH) $\lambda_{max}$: 280 nm($\epsilon$=2.8×10$^4$); $^1$H-NMR(DMSO-d$_6$) $\delta$:1.33(t,3H,—CH$_2$CH$_2$CH$_3$), 2.47(s,6H,C-3—CH$_3$ and C-4—CH$_3$), 4.52(m,4H,—CH$_2$CH$_2$—), 5.72(s,1H,C-5—H); MS, m/z: 222(M$^+$). Anal. Calcd for C$_{11}$H$_{14}$N$_2$O$_3$: C, 59.45; H, 6.35; N, 12.60. Found: C, 59.39; H, 6.31; N, 12.68.

EXAMPLE 1-5

5-bromo-2-hydroxyethyl-3,4-dimethylpyrano[2,3-c]pyrazol-6(1H)-one (II-5)

The synthesis and purification procedures for preparing compound II-1 as described in Example 1-1 were repeated to obtain compound II-5 except that 2-hydroxyethyl-3,4-dimethylpyrano[2,3-c]pyrazol-6(1H)-one (I-5) (5 g, 0.024 mol) was used instead of compound I-1. Compound II-5 obtained is in the form of white crystal. Yield, 4.8 g (70%).

mp: 152°–153° C.; IR(KBr) $\nu_{max}$: 3500–2500(—OH)cm$^{-1}$,1720(C=O)cm$^{-1}$; UV(C$_2$H$_5$OH) $\lambda_{max}$: 301 nm($\epsilon$=4.4×10$^4$); $^1$H-NMR(DMSO-d$_6$) $\delta$:2.36(s,6H,C-3—CH$_3$ and C-4—CH$_3$), 3.72 (t,2H,—NCH$_2$—), 3.98(t,2H,—CH$_2$OH), 4.70(br,1H,OH), 5.72(m,1H,C-5—H); MS, m/z: 287(M$^+$). Anal. Calcd for C$_{10}$H$_{11}$BrN$_2$O$_3$: C, 41.83; H, 3.86; N, 9.76. Found: C, 41.70; H, 3.82; N, 9.86.

2-hydroxyethyl-3,4-dimethylfuro[2,3-c]pyrazole-5-carboxylic acid (III-5)

The synthesis and purification procedures for preparing compound III-1 as described in Example 1-1 were repeated to obtain compound III-5 except that compound II-5 (5 g, 0.015 mol) was used instead of compound II-1. Compound III-5 obtained is in the form of white crystal. Yield, 1.7 g (35%).

mp: 203°–206° C.; IR(KBr) $\nu_{max}$: 2500–3000(—OH)cm$^{-1}$,1680(C=O)cm$^{-1}$; UV(C$_2$H$_5$OH) $\lambda_{max}$: 283 nm($\epsilon$=3.2×10$^4$); $^1$H-NMR(DMSO-d$_6$) $\delta$:2.45(s,6H,C-3—CH$_3$ and C-4—CH$_3$), 3.71(t,2H,—NCH$_2$—), 4.08(t,2H,—CH$_2$OH), 4.83(t,1H,OH), 5.72(m,1H,C-5—H); MS, m/z: 224(M$^+$). Anal. Calcd for C$_{10}$H$_{12}$N$_2$O$_4$: C, 53.57; H, 5.39; N, 12.49. Found: C, 53.60; H, 5.41; N, 12.53.

EXAMPLE 1-6

5-bromo-2-benzyl-3,4-dimethylpyrano[2,3-c]pyrazol-6(1H)-one (II-6)

The synthesis and purification procedures for preparing compound II-1 as described in Example 1-1 were repeated to obtain compound II-6 except that 2-hydroxyethyl-3,4-dimethylpyrano[2,3-c]pyrazol-6(1H)-one (I-5) (5 g, 0.020 mol) was used instead of compound I-1. Compound II-6 obtained is in the form of white crystal. Yield, 5.4 g (81%).

mp: 176°–177° C.; IR(KBr) $\nu_{max}$: 1720(C=O)cm$^{-1}$; UV(CHCl$_3$) $\lambda_{max}$: 317.5 nm($\epsilon$=1.6×10$^4$); $^1$H-NMR(CDCl$_3$) $\delta$:2.43(s,3H,C-4—CH$_3$), 2.50(s,3H,C-3—CH$_3$), 5.43(s,2H,—CH$_2$—C$_6$H$_5$), 7.25(m,5H,—CH$_2$—C$_6$H$_5$); MS, m/z: 332(M$^+$). Anal. Calcd for C$_{15}$H$_{13}$BrN$_2$O$_2$: C, 54.07; H, 3.93; N, 8.41. Found: C, 54.15; H, 3.81; N, 8.40.

2-benzyl-3,4-dimethylfuro[2,3-c]pyrazole-5-carboxylic acid (III-6)

The synthesis and purification procedures for preparing compound III-1 as described in Example 1-1 were repeated to obtain compound III-6 except that compound II-6 (5 g, 0.015 mol) was used instead of compound II-1. Compound III-6 obtained is in the form of yellow brown crystal. Yield, 3.2 g (81%).

mp: 196°–198° C.; IR(KBr) $\nu_{max}$: 2250–3300(O—H); 1720(C=O)cm$^{-1}$; UV(C$_2$H$_5$OH) $\lambda_{max}$: 284.5 nm($\epsilon$:2.2×10$^4$); $^1$H-NMR(DMSO-d$_6$) $\delta$:2.47(s,6H,C-3—CH$_3$,C-4—CH$_3$), 5.37(s,2H,—CH$_2$—C$_6$H$_5$), 7.25(m,5H,—CH$_2$—C$_6$H$_5$); MS, m/z: 270(M$^+$). Anal. Calcd for C$_{15}$H$_{14}$N$_2$O$_3$: C, 66.66, H, 5.22; N, 10.36. Found: C, 66.73; H, 5.29; N, 10.47.

EXAMPLE 1-7

5-bromo-2-(2-chlorophenylmethyl)-3,4-dimethylpyrano[2,3-c]pyrazol-6(2H)-one (II-7)

To a solution of 2-(2-chlorophenylmethyl)-3,4-dimethylpyrano[2,3c]pyrazol-6(2H)-one (I-7) (5.0 g, 0.017 mol) in 100 ml of chloroform, a bromine-chloroform solution which was prepared by dissolving bromine (5.0 g, 0.031 mol) in 50 ml chloroform was added dropwise and slowly at room temperature. After the reaction was completed, sodium bisulfite was added until the color of the reaction mixture turn to colorless. The reaction mixture was then filtered, and the filtrate was washed with water until acidless. The chloroform layer was dried with anhydrous magnesium sulfate, and it was then filtered again. After the solvent medium was removed from the filtrate by evaporation under reduced pressure, the residue was recrystallized from chloroform-ethanol to give compound II-7 in the form of white needle crystal. Yield, 5.95 g (95.1%).

mp: 206°–208° C.; IR(KBr) $\nu_{max}$: 1712(C=O)cm$^{-1}$; UV(CHCl$_3$) $\lambda_{max}$: 318 nm($\epsilon$=2.47×10$^4$); $^1$H-NMR(CDCl$_3$) $\delta$:2.482(s,3H,C-4—CH$_3$), 2.55(s,3H,C-3—CH$_3$), 5.40(s,2H,—CH$_2$—), 6.82(t,1H,5'—H), 7.12–7.46(m,3H,3',4' and 6'—H); MS, m/z: 368(M$^+$). Anal. Calcd for C$_{15}$H$_{12}$BrClN$_2$O$_2$: C, 49.01; H, 3.29; N, 7.62. Found: C, 49.20; H, 3.35, N: 7.69.

2-(2-chlorophenylmethyl)-3,4-dimethylfuro[2,3-c]pyrazole-5(2H)-carboxylic acid (III-7)

Metal sodium (1.00 g, 0.043 mol) was dissolved in 400 ml of n-butanol to get sodium butoxide solution. Compound II-7 (5.0 g, 0.014 mol) was dissolved in butanol, and the temperature of the solution was raised to and maintained at 120° C., followed by adding the sodium butoxide solution dropwise and slowly. After the reaction was completed, the solvent of the reaction mixture was distilled off under reduced pressure. The residue was dissolved in water, and was acidified with 1N HCl solution. The precipitate formed by acidification was collected by filtration and was recrystallized from methanol to get compound III-7 in the form of light yellow crystal. Yield, 1.66 g (39.0%).

mp: 218° C.(dec.); IR (KBr) $\nu_{max}$: 2300–3100(O—H), 1663 (C=O)cm$^{-1}$; UV(C$_2$H$_5$OH) $\lambda_{max}$: 280 nm($\epsilon$=1.82×10$^4$); $^1$H-NMR(DMSO-d$_6$) $\delta$:2.48(s,3H,C-4—CH$_3$), 2.50(s,3H,C-3—CH$_3$), 5.44(s,2H,—CH$_2$—), 6.79(t,1H,5'—H), 7.25–7.55(m,3H,3',4' & 6'—H); MS, m/z: 304(M$^+$). Anal. Calcd for C$_{15}$H$_{13}$ClN$_2$O$_3$: C, 59.12; H, 4.30; N, 9.19. Found: C, 59.25; H, 4.34; N, 9.20.

EXAMPLE 1-8

5-bromo-2-(3-chlorophenylmethyl)-3,4-dimethylpyrano[2,3-c]-pyrazol-6(2H)-one (II-8)

The synthesis and purification procedures for preparing compound II-1 as described in Example 1-1 were repeated to obtain compound II-8 except that 2-(3-chlorophenylmethyl)-3,4-dimethylpyrano[2,3-c]-pyrazol-6(2H)-one (I-8) (5.0 g, 0.017 mol) was used instead of compound I-1. Compound II-8 obtained is in the form of light yellow crystal. Yield, 5.78 g (92.4%).

mp: 148°–149° C.; IR(KBr) $\nu_{max}$: 1712(C=O)cm$^{-1}$; UV (CHCl$_3$) $\lambda_{max}$: 318 nm($\epsilon$=1.66×10$^4$); $^1$H-NMR(DMSO-d$_6$) $\delta$:2.53(d,3H,J=1.2 Hz,C-4—CH$_3$), 2.56(s,3H,C-3—CH$_3$), 5.41(s,2H,—CH$_2$—), 7.16–7.42(m,4H, benzene ring protons); MS, m/z: 368(M$^+$). Anal. Calcd for C$_{15}$H$_{12}$BrClN$_2$O$_2$: C, 49.01; H, 3.29; N, 7.62. Found: C, 49.18; H, 3.20; N, 7.54.

2-(3-chlorophenylmethyl)-3,4-dimethylfuro[2,3-c]pyrazole-5(2H)-carboxylic acid (III-8)

The synthesis and purification procedures for preparing compound III-1 as described in Example 1-1 were repeated to obtain compound III-8 except that compound II-8 (5.0 g, 0.014 mol) was used instead of compound II-1. Compound III-8 obtained is in the form of yellow crystal. Yield, 2.42 g (56.9%).

mp: 204° C.(dec.); IR (KBr) $\nu_{max}$: 2000–3200(O—H), 1665 (C=O)cm$^{-1}$; UV(C$_2$H$_5$OH) $\lambda_{max}$: 280 nm($\epsilon=1.98\times10^4$); $^1$H-NMR(DMSO-d$_6$) δ:2.48(s,6H,C-3 and C-4—CH$_3$), 5.41(s,2H,—CH$_2$—), 7.12–7.41(m,4H, benzene ring protons); MS, m/z: 304(M+). Anal. Calcd for C$_{15}$H$_{13}$ClN$_2$O$_3$: C, 59.12; H, 4.30; N, 9.19. Found: C, 59.36; H, 4.28; N, 9.11.

EXAMPLE 1-9

5-bromo-2-(4-chlorophenylmethyl)-3,4-dimethylpyrano[2,3-c]-pyrazol-6(2H)-one (II-9)

The synthesis and purification procedures for preparing compound II-1 as described in Example 1-1 were repeated to obtain compound II-9 except that 2-(4-chlorophenylmethyl)-3,4-dimethylpyrano[2,3-c]-pyrazol-6(2H)-one (I-9) (5.0 g, 0.017 mol) was used instead of compound I-1. Compound II-9 obtained is in the form of light yellow crystal. Yield, 5.60 g (89.5%).

mp: 149°–152° C.; IR (KBr) $\nu_{max}$: 1715(C=O)cm$^{-1}$; UV(CHCl$_3$) $\lambda_{max}$: 316 nm($\epsilon=1.58\times10^4$); $^1$H-NMR(CDCl$_3$) δ:2.46(d,3H,J=1.2Hz,C-4—CH$_3$), 2.51(s,3H,C-3—CH$_3$), 5.26(s,2H,—CH$_2$—), 7.08(d,2H,J=8.4 Hz,2' and 6'—H), 7.30(d,2H,J=8.4 Hz,3' &5'—H); MS, m/z: 368(M+). Anal. Calcd for C$_{15}$H$_{12}$BrClN$_2$O$_2$: C, 49.01; H, 3.29; N, 7.62. Found: C, 49.21; H, 3.18; N, 7.71.

2-(4-chlorophenylmethyl)-3,4-dimethylfuro[2,3-c]pyrazole-5(2H)-carboxylic acid (III-9)

The synthesis and purification procedures for preparing compound III-1 as described in Example 1-1 were repeated to obtain compound III-9 except that compound II-9 (5.0 g, 0.014 mol) was used instead of compound II-1. Compound III-9 obtained is in the form of white crystal. Yield, 1.51 g (35.5%).

mp: 218° C.(dec.); IR (KBr) $\nu_{max}$: 2400–3600(O—H), 1685(C=O)cm$^{-1}$; UV(C$_2$H$_5$OH) $\lambda_{max}$: 282 nm($\epsilon=2.83\times10^4$); $^1$H-NMR(DMSO-d$_6$) δ:2.47(s,3H,C-4—CH$_3$), 2.48(s,3H,C-3—CH$_3$), 5.38(s,2H,—CH$_2$—), 7.19(d,2H,J=8.6 Hz,2' &6'—H), 7.41(d,2H,J=8.6 Hz,3' & 5'—H); MS, m/z: 304(M+). Anal. Calcd for C$_{15}$H$_{13}$ClN$_2$O$_3$: C, 59.12, H:4.30; N, 9.19. Found: C, 59.24; H, 4.26; N, 9.10.

EXAMPLE 1-10

5-bromo-2-(2-methoxyphenylmethyl)-3,4-dimethylpyrano[2,3-c]-pyrazo-6(2H)-one (II-10)

The synthesis and purification procedures for preparing compound II-1 as described in Example 1-1 were repeated to obtain compound II-10 except that 2-(2-methoxyphenylmethyl)-3,4-dimethylpyrano[2,3-c]-pyrazo-6(2H)-one (I-10) (5.0 g, 0.018 mol) was used instead of compound I-1. Compound II-10 obtained is in the form of white crystal. Yield, 6.05 g (92.6%).

mp: 212°–214° C.; IR (KBr) $\nu_{max}$: 1721(C=O)cm$^{-1}$; UV(CHCl$_3$) $\lambda_{max}$: 320 nm($\epsilon=1.85\times10^4$); $^1$H-NMR(CDCl$_3$) δ:2.49(s,3H,C-4—CH$_3$), 2.52(s,3H,C-3—CH$_3$), 3.87(s,3H,—OCH$_3$), 5.29(s,2H,—CH$_2$—), 6.83–6.91(m,3H,3',5' &6'—H), 7.18–7.37(m,1H,4'—H); MS, m/z: 363(M+). Anal. Calcd for C$_{16}$H$_{15}$BrN$_2$O$_3$: C, 52.91; H, 4.16; N, 7.71. Found: C, 52.95; H, 4.20; N, 7.68.

2-(2-methoxyphenylmethyl)-3,4-dimethylfuro[2,3-c]pyrazole-5(2H)-carboxylic acid (III-10)

The synthesis and purification procedures for preparing compound III-1 as described in Example 1-1 were repeated to obtain compound III-10 except that compound II-10 (5.0 g, 0.014 mol) was used instead of compound II-1. Compound III-10 obtained is in the form of light yellow crystal. Yield, 3.01 g (71.7%).

mp: 170° C.(dec.); IR (KBr) $\nu_{max}$: 2050–3600(O—H), 1685(C=O)cm$^{-1}$; UV(C$_2$H$_5$OH) $\lambda_{max}$: 280 nm($\epsilon=1.53\times10^4$); $^1$H-NMR(DMSO-d$_6$) δ:2.37(s,3H,C-4—CH$_3$), 2.43(s,3H,C-3—CH$_3$), 3.84(s,3H,—OCH$_3$), 5.22(s,2H,—CH$_2$—), 6.60(d,1H,3'—H), 6.88(t,1H,5'—H), 7.01(d,1H,6'—H), 7.27(t,1H,4'—H); MS, m/z: 300(M+). Anal. Calcd for C$_{16}$H$_{16}$N$_2$O$_4$: C, 63.99; H, 5.37; N, 9.93. Found: C, 63.80; H, 5.31, N, 9.83.

EXAMPLE 1-11

5-bromo-2-(3-methoxyphenylmethyl)-3,4-dimethylpyrano[2,3-c]-pyrazol-6(2H)-one (II-11)

The synthesis and purification procedures for preparing compound II-1 as described in Example 1-1 were repeated to obtain compound II-11 except that 2-(3-methoxyphenylmethyl)-3,4-dimethylpyrano[2,3-c]pyrazol-6(2H)-one (I-11) (5.0 g, 0.018 mol) was used instead of compound I-1 and a column chromatography (silicagel, chloroform) was run before recrystalization). Compound II-11 obtained is in the form of white crystal. Yield, 6.12 g (93.7%).

mp: 148°–151° C.; IR (KBr) $\nu_{max}$: 1712(C=O)cm$^{-1}$; UV(CHCl$_3$) $\lambda_{max}$: 318 nm($\epsilon=2.07\times10^4$); $^1$H-NMR(CDCl$_3$) δ:2.46(d,3H,C-4—CH$_3$), 2.51(s,3H,C-3—CH$_3$), 3.76(s,3H,—OCH$_3$), 5.26(s,2H,—CH$_2$—), 6.66–6.87(m,3H,2' &4' &6'—H), 7.25(t,1H,5'—H); MS, m/z: 363(M+). Anal. Calcd for C$_{16}$H$_{15}$BrN$_2$O$_3$: C, 52.91; H, 4.16; N, 7.71. Found: C, 52.80; H, 4.11; N, 7.80.

2-(3-methoxyphenylmethyl)-3,4-dimethylpyrano[2,3-c]pyrazol-5(2H)-carboxlic acid (III-11)

The synthesis and purification procedures for preparing compound III-1 as described in Example 1-1 were repeated to obtain compound III-11 except that compound II-11 (5.0 g, 0.014 mol) was used instead of compound II-1. Compound III-11 obtained is in the form of yellow crystal. Yield, 1.26 g (30.0%).

mp: 214° C.(dec.); IR (KBr) $\nu_{max}$: 2000–3200(O—H 1707(C=O)cm$^{-1}$; UV(CHCl$_3$) $\lambda_{max}$: 292 nm($\epsilon=1.68\times10^4$); $^1$H-NMR(MeOH-d$_4$) δ:2.44(s,3H,C-4—CH$_3$), 2.52(s,3H,C-3—CH$_3$), 3.69(s,3H,—OCH$_3$), 5.34(s,2H,—CH$_2$—), 6.19–6.85(m,3H,2' &4' &6'—H), 7.13–7.53(m,1H,5'—H); MS, m/z: 300(M+). Anal. Calcd for C$_{16}$H$_{16}$N$_2$O$_4$: C, 63.99; H, 5.37, N, 9.93. Found: C, 63.91; H, 5.32; N, 10.03.

EXAMPLE 1-12

5-bromo-2-(4-methoxyphenylmethyl)-3,4-dimethylpyrano[2,3-c]pyrazol-6(2H)-one (II-12)

The synthesis and purification procedures for preparing compound II-1 as described in Example 1-1 were repeated to obtain compound II-12 except that 2-(4-methoxyphenylmethyl)-3,4-dimethyl-pyrano[2,3-c]pyrazol-6(2H)-one (I-12) (5.0 g, 0.018 mol) was used instead of compound I-1. Compound II-12 obtained is in the form of white crystal. Yield, 6.18 g (94.6%).

mp: 169°–172° C.; IR(KBr) $\nu_{max}$: 1712(C=O)cm$^{-1}$; UV(CHCl$_3$) $\lambda_{max}$: 320 nm($\epsilon$=2.83×10$^4$); $^1$H-NMR(CDCl$_3$) $\delta$:2.47(d,3H,C-4—CH$_3$), 2.50(s,3H,C-3—CH$_3$), 3.77(s,3H,—OCH$_3$), 5.22(s,2H,—CH$_2$—), 6.83(d,2H,J=8.8 Hz,3' &5'—H), 7.12(d,2H,J=8.8 Hz,2' &6'—H); MS, m/z: 363(M$^+$). Anal. Calcd for C$_{16}$H$_{15}$BrN$_2$O$_3$: C, 52.91; H, 4.16; N, 7.71. Found: C, 52.79; H, 4.01; N, 7.63.

2-(4-methoxyphenylmethyl)-3,4-dimethylfuro[2,3-c]-pyrazole-5(2H)-carboxylic acid (III-12)

The synthesis and purification procedures for preparing compound III-1 as described in Example 1-1 were repeated to obtain compound III-12 except that compound II-12 (5.0 g, 0.014 mol) was used instead of compound II-1 and ethyl acetate-methanol was used instead of ethanol in the recrystalization step. Compound III-12 obtained is in the form of light yellow crystal. Yield, 3.37 g (80.2%).

mp: 210° C.(dec.); IR (KBr) $\nu_{max}$: 2050–3300(O—H), 1667 (C=O)cm$^{-1}$; UV (C$_2$H$_5$OH) $\lambda_{max}$: 282 nm($\epsilon$=2.80×10$^4$); $^1$H-NMR(MeOH-d$_4$) $\delta$:2.36(s,3H,C-4—CH$_3$), 2.50(s,3H,C-3—CH$_3$), 3.71(s,3H,—OCH$_3$), 5.21(s,2H,—CH$_2$—), 6.80(d,2H,3' &5'—H), 7.06(d,2H,2' &6'—H); MS, m/z: 300(M$^+$). Anal. Calcd for C$_{16}$H$_{16}$N$_2$O$_4$: C, 63.99; H, 5.37; N, 9.93. Found: C, 63.89; H, 5.42; N, 9.90.

EXAMPLE 1-13

5-bromo-2-(3,4-dimethoxyphenylmethyl)-3,4-dimethyl-pyrano[2,3-c]pyrazol(2H)-one (II-13)

The synthesis and purification procedures for preparing compound II-1 as described in Example 1-1 were repeated to obtain compound II-13 except that 2-(3,4-dimethoxyphenylmethyl)-3,4-dimethyl-pyrano[2,3-c]pyrazol(2H)-one (I-13) (5.0 g, 0.016 mol ) was used instead of compound I-1. Compound II-13 obtained is in the form of white crystal. Yield, 6.17 g (98.1%).

mp: 177°–180° C.; IR (KBr) $\nu_{max}$: 1712(C=O)cm$^{-1}$; UV(CHCl$_3$) $\lambda_{max}$: 318 nm($\epsilon$=2.28×10$^4$); $^1$H-NMR(CDCl$_3$) $\delta$:2.48(s,3H,C-4—CH$_3$), 2.50(s,3H,C-3—CH$_3$), 3.83&3.85(s,6H,2x—OCH$_3$), 5.22(s,2H,—CH$_2$—), 6.73–6.87(m,3H, benzene ring protons); MS, m/z: 393(M$^+$). Anal. Calcd for C$_{17}$H$_{17}$BrN$_2$O$_4$: C, 51.92; H, 4.36; N, 7.12. Found: C, 51.85; H, 4.31; N, 7.08.

2-(3,4-dimethoxyphenylmethyl)-3,4-dimethyl-furo[2,3-c]pyrazole-5(2H)-carboxylic acid (III-13)

The synthesis and purification procedures for preparing compound III-1 as described in Example 1-1 were repeated to obtain compound III-13 except that compound II-13 (5.0 g, 0.013 mol) was used instead of compound II-1. Compound III-13 obtained is in the form of white crystal. Yield, 1.20 g (28.0%).

mp: 182° C.(dec.); IR (KBr) $\nu_{max}$: 2200–3600(O—H), 1682(C=O)cm$^{-1}$; UV(CHCl$_3$) $\lambda_{max}$: 290 nm($\epsilon$=2.21×10$^4$); $^1$H-NMR(DMSO-d$_6$) $\delta$:2.47(s,6H,2x—CH$_3$), 3.72(s,6H,2x—OCH$_3$), 5.28(s,2H,—CH$_2$—), 6.67(m,1H,6'—H), 6.86–6.95(m,2H,2'&5'—H); MS, m/z: 330(M$^+$). Anal. Calcd for C$_{17}$H$_{18}$N$_2$O$_5$: C, 61.18; H, 5.49; N, 8.48. Found: C, 61.0; H, 5.40; N, 8.56.

EXAMPLE 1-14

5-bromo-2-(2-thienylmethyl)-3,4-dimethylpyrano-[2,3-c]pyrazol-6(2H)-one (II-14)

The synthesis and purification procedures for preparing compound II-1 as described in Example 1-1 were repeated to obtain compound II-14 except that 2-(2-thienylmethyl)-3,4-dimethylpyrano[2,3-c]pyrazol-6(2H)-one (I-14) (5.0 g, 0.019 mol) was used instead of compound I-1. Compound II-14 obtained is in the form of white crystal. Yield, 6.25 g (97.0%).

mp: 164°–167° C.; IR (KBr) $\nu_{max}$: 1713(C=O)cm$^{-1}$; UV(CHCl$_3$) $\lambda_{max}$: 318 nm($\epsilon$=2.24×10$^4$); $^1$H-NMR(DMSO-d$_6$) $\delta$:2.51(s,3H,C-4—CH$_3$), 2.60(s,3H,C-3—CH$_3$), 5.55(s,2H,—CH$_2$—), 6.95–7.16(m,2H,3'&-4'—H), 7.47(dd,1H,J=1.2 Hz,J=4.7 Hz, 5'—H); MS, m/z: 339(M$^+$). Anal. Calcd for C$_{13}$H$_{11}$BrN$_2$O$_2$S: C, 46.03; H, 3.27; N, 8.26. Found: C, 46.15; H, 3.36; N, 8.40.

2-(2-thienylmethyl)-3,4-dimethylfuro[2,3-c]pyrazole-5(2H)-carboxylic acid (III-14)

The synthesis and purification procedures for preparing compound III-1 as described in Example 1-1 were repeated to obtain compound III-14 except that compound II-14 (5.0 g, 0.019 mol) was used instead of compound II-1. Compound III-14 obtained is in the form of light yellow crystal. Yield, 2.33 g (56.3%).

mp: 189° C.(dec.); IR (KBr) $\nu_{max}$: 2200–3500(O—H), 1707(C=O)cm$^{-1}$; UV(C$_2$H$_5$OH) $\lambda_{max}$: 280 nm($\epsilon$=1.66×10$^4$); $^1$H-NMR(DMSO-d$_6$) $\delta$:2.46(s,3H,C-4—CH$_3$), 2.52(s,3H,C-3—CH$_3$), 5.55(s,2H,—CH$_2$—), 6.93–7.13(m,2H,3'&4'—H), 7.46(dd,1H,5'—H); MS, m/z: 276(M$^+$). Anal. Calcd for C$_{13}$H$_{12}$N$_2$O$_3$S: C, 56.51; H, 4.38; N, 10.14. Found: C, 56.62; H, 4.42; N, 10.19.

EXAMPLE 1-15

5-bromo-2-(2-pyridylmethyl)-3,4-dimethylpyrano[2,3-c]pyrazol-6(2H)-one (II-15)

To a solution of 2-(2-pyridylmethyl)-3,4-dimethyl-pyrano-[2,3-c]pyrazol-6(2H)-one (I-15) (5.0 g, 0.020 mol) in 100 ml of chloroform, a bromine-chloroform solution which was prepared by dissolving bromine (5.0 g, 0.031 mol) in 50 ml chloroform was added dropwise and slowly at room temperature. After the reaction was completed, sodium bisulfite was added until the color of the reaction mixture turn to colorless. The reaction mixture was then filtered, and the filtrate was collected. The precipitate was mixed with 400 ml of water to dissolve the excess sodium bissulfite. The insoluable substance was washed with 10% sodium carbonate solution and dissolved with chloroform. The resulting chloroform solution was combined with the filtrate, then was washed with water for several times. The chloroform layer was dried with anhydrous magnesium sulfate, and it was then filtered again. After the solvent medium was removed from the filtrate by evaporation under reduced pressure, the residue was recrystalized from chloroform-ethanol to give compound II-15 in light yellow prismatic crystal form. Yield, 6.52 g (97.3%).

mp: 179°–182° C.; IR (KBr) $\nu_{max}$: 1715(C=O)cm$^{-1}$; UV(CHCl$_3$) $\lambda_{max}$: 318 nm($\epsilon$=1.34×10$^4$); $^1$H-NMR(CDCl$_3$) $\delta$:2.52(s,3H,C-4—CH$_3$), 2.56(s,3H,C-3—CH$_3$), 5.40(s,2H,—CH$_2$—), 7.07–7.33(m,2H,3'&-4'—H), 7.67(dt,1H,J=1.9 Hz,J=7.6 Hz,4'—H), 8.53(d,1H,6'—H); MS, m/z: 335(M$^+$). Anal. Calcd for C₁₄H₁₂BrN₃O₂: C, 50.32; H, 3.62; N, 12.57. Found: C, 50.39; H, 3.49; N, 12.62.

2-(2-pyridylmethyl)-3,4-dimethylfuro[2,3-c]pyrazole-5(2H)-carboxylic acid (III-15)

The synthesis and purification procedures for preparing compound III-1 as described in Example 1-1 were repeated to obtain compound III-15 except that compound II-15 (5.0 g, 0.015 mol) was used instead of compound II-1. Compound III-15 obtained is in yellow crystal form. Yield, 3.55 g (87.3%).

mp: 192° C.(dec.); IR (KBr) $\nu_{max}$: 2100-3550(O—H), 1682(C=O)cm⁻¹; UV(C₂H₅OH) $\lambda_{max}$: 282 nm($\epsilon$=2.20×10⁴); ¹H-NMR(MeOH-d₄) δ:2.51(s,3H,C-4—CH₃), 2.54(s,3H,C-3—CH₃), 5.46(s,2H,—CH₂—), 7.05(d,1H,3'—H), 7.31(t,1H,5'—H), 7.78(dt,1H,4'—H), 8.50(d,1H,6'—H); MS, m/z: 271(M⁺). Anal. Calcd for C₁₄H₁₃N₃O₃: C, 61.99; H, 4.83, N, 15.49. Found: C, 61.85; H, 4.89; N, 15.54.

EXAMPLE 1-16

5-bromo-2-(3-pyridylmethyl)-3,4-dimethylpyrano[2,3-c]pyrazole-6(2H)-one (II-16)

The synthesis and purification procedures for preparing compound II-1 as described in Example 1-1 were repeated to obtain compound II-16 except that 2-(3-pyridylmethyl)-3,4-dimethylpyrano[2,3-c]pyrazole-6(2H)-one (I-16) (5.0 g, 0.020 mol) was used instead of compound I-1. Compound II-16 obtained is in the form of white crystal. Yield, 6.40 g (95.5%).

mp: 191°-193° C.; IR (KBr) $\nu_{max}$: 1715(C=O)cm⁻¹; UV(CHCl₃) $\lambda_{max}$: 316 nm($\epsilon$=2.18×10⁴); ¹H-NMR(CDCl₃) δ:2.51(s,3H,C-4—CH₃), 2.52(s,3H,C-3—CH₃), 5.32(s,2H,—CH₂—), 7.28(t,1H,5'—H), 7.54(d,1H,4'—H), 8.55(m,2H,2'&6'—H); MS, m/z: 335(M⁺). Anal. Calcd for C₁₄H₁₂BrN₃O₂: C, 50.32; H, 3.62; N, 12.57. Found: C, 50.44, H: 3.49; N, 12.63.

2-(3-pyridylmethyl)-3,4-dimethylfuro[2,3-c]pyrazole-5(2H)-carboxylic acid (III-16)

The synthesis and purification procedures for preparing compound III-1 as described in Example 1-1 were repeated to obtain compound III-16 except that compound II-16 (5.0 g, 0.015 mol) was used instead of compound II-1. Compound III-16 obtained is in yellow crystal form. Yield, 3.00 g (73.8%).

mp: 214° C.(dec.);IR (KBr) $\nu_{max}$: 2100-3600(O—H), 1687(C=O)cm⁻¹; UV(C₂H₅OH) $\lambda_{max}$: 280 nm($\epsilon$=2.62×10⁴); ¹H-NMR(DMSO-d₆) δ:2.48(s,3H,C-4—CH₃), 2.51(s,3H,C-3—CH₃), 5.44(s,2H,—CH₂—), 7.36(t,1H,5'—H), 7.58(d,1H4'—H), 8.47-8.49(m,2H,2'&6'—H); MS, m/z: 271(M⁺). Anal. Calcd for C₁₄H₁₃N₃O₃: C, 61.99; H, 4.83; N, 15.49. Found: C, 62.03; H, 4.92; N, 15.54.

EXAMPLE 1-17

5-bromo-2-(4-pyridylmethyl)-3,4-dimethylpyrano[2,3-c]pyrazol-6(2H)-one (II-17)

The synthesis and purification procedures for preparing compound II-1 as described in Example 1-1 were repeated to obtain compound II-17 except that 2-(4-pyridylmethyl)-3,4-dimethylpyrano[2,3-c]pyrazol-6(2H)-one (I-17) (5.0 g, 0.020 mol) was used instead of compound I-1. Compound II-17 obtained is in the form of light yellow crystal. Yield, 6.45 g (96.3%).

mp: 177°-180° C.; IR (KBr) $\nu_{max}$: 1712(C=O)cm⁻¹; UV(CHCl₃) $\lambda_{max}$: 316 nm($\epsilon$=1.47×10⁴); ¹H-NMR(CDCl₃) δ:2.47(s,3H,C-4—CH₃), 2.53(s,3H,C-3—CH₃), 5.33(s,2H,—CH₂—), 7.02(d,2H,J=6.1 Hz, 3'&5'—H), 8.57(dd,2H,J=1.5 Hz, 2'&6'—H); MS, m/z: 335(M⁺). Anal. Calcd for C₁₄H₁₂BrN₃O₂: C, 50.32; H, 3.62; N, 12.57. Found: C, 50.28; H, 3.51; N, 12.39.

2-(4-pyridylmethyl)-3,4-dimethylfuro[2,3-c]pyrazole-5(2H)-carboxylic acid (III-17)

The synthesis and purification procedures for preparing compound III-1 as described in Example 1-1 were repeated to obtain compound III-17 except that compound II-17 (5.0 g, 0.015 mol) was used instead of compound II-1. Compound III-17 obtained is in yellow crystal form. Yield, 2.20 g (54.1%).

mp: 228° C.(dec.); IR (KBr) $\nu_{max}$: 2100-3600(O—H), 1685(C=O)cm⁻¹; UV(C₂H₅OH) $\lambda_{max}$: 280 nm($\epsilon$=1.65×10⁴); ¹H-NMR(meOH-d₄) δ:2.51(s,3H,C-4—CH₃), 2.59(s,3H,C-3—CH₃), 5.50(s,2H,—CH₂—), 7.07(d,2H,3'&5'—H), 8.52(d,2H,2'&6'—H); MS, m/z: 271(M⁺). Anal. Calcd for C₁₄H₁₃N₃O₃: C, 61.99; H, 4.83; N, 15.49. Found: C, 61.85; H, 4.68; N, 15.30.

Scheme 3
Part two: preparation of 2-,3-,4-trisubstituted furo[2,3-c]pyrazole-5-carboxaldehydes (V)

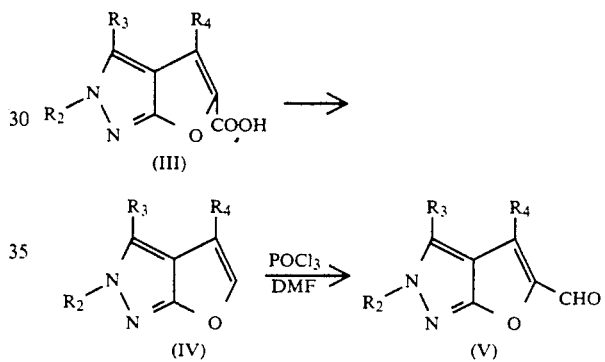

wherein R₂, R₃ and R₄ represent the same meanings as defined above.

As shown in Scheme 3, compound III was dissolved in a suitable solvent (e.g. quinoline) and the resulting solution was heated in the presence of a metalic catalyst (e.g. active copper) to carry out decarboxylic acid reaction. After the reaction was completed, the product was purified by column chromatography and recrystalization to give the corresponding 2,3,4-trisubstituted furo[2,3-c]pyrazole (IV). This compound IV was dissolved in an suitable solvent (e.g. DMF) and Vielsmieir formylation was conducted give the desired 2,3,4-trisubstituted furo[2,3-c]pyrazole-5-carboxaldehydes (V).

EXAMPLE 2-1

2,3,4-trimethylfuro[2,3-c]pyrazole(IV-1)

Cupric sulfate (10.0 g) was dissolved in water and zinc powder (3.0 g) was added to the solution stepwise to form precipitate. The precipitate was collected by filtration and washed with 10% HCl solution, then washed with water and dried to obtain the desired active copper.

The compound III-1 (5.0 g, 0.026 mol) was dissolved in dry quinoline (60 ml), and the active copper (1.0 g, 0.016 mol) was added, which was then heated and maintained at 200° C. for 30 min while stirring. After the reaction was completed, the reaction mixture was cooled to room temperature and acidified with 10% HCl solution, and then filtered. The filtrate was extracted with cholroform, and the chloroform layer was washed with water for several times, dried with anhydrous magnesium sulfate to remove water therefrom, and filtered. The solvent medium was removed from the filtrate by evaporation under reduced pressure, and the residue was purified by column chromatography (silica gel-chloroform) to give compound IV-1 in light brown crystal form. Yield, 0.25 g (6.5%).

mp: 68°–71° C.; UV (CHCl$_3$) $\lambda_{max}$: 249 nm; $^1$H-NMR(CDCl$_3$) δ:2.06(s,3H,C-4—CH$_3$), 2.33(s,3H,C-3—CH$_3$), 3.37(s,3H,N—CH$_3$), 6.86(s,1H,C-5—H); MS, m/z: 150(M+). Anal. Calcd for C$_8$H$_{10}$N$_2$O: C, 63.98; H, 6.71; N, 18.65. Found: C, 63.79; H, 6.75; N, 18.54.

5-formyl-2,3,4-trimethylfuro[2,3-c]pyrazole (V-1)

N,N-dimethylformamide, DMF, (30 g, 0.41 mol) was added dropwise and slowly to phosphoryl chloride (10 g, 0.065 mol) at 5°–10° C. while stirring, and the solution was stirred at 10° C. for additional 20 minutes. To the solution, a solution of compound IV-1 (1.0 g, 0.0067 mole) in dimethylformamide (20 ml) was added dropwise and slowly at 0°–5° C. while stirring, and maintained stirring at room temperature for additional 30 minutes. The reaction mixture was poured into ice water, which was then neutrized with sodium carbonate and settled at room temperature for 8 hours. The solution was extracted with cholroform, and the chloroform layer was dried with anhydrous magnesium sulfate to remove water therefrom, and filtered. The solvent medium was removed from the filtrate by evaporation under reduced pressure, and the residue was purified by column chromatography (silica gel-chloroform) to give compound V-1 in light yellow crystal form. Yield, 0.95 g (80%).

mp: 122°–124° C.; IR (KBr) $\nu_{max}$: 1645(C=O)cm$^{-1}$; UV(CHCl$_3$) $\lambda_{max}$: 320 nm; $^1$H-NMR(CDCl$_3$) δ:2.50(s,3H,C-3—CH$_3$), 2.53(s,3H,C-4—CH$_3$), 3.86(s,3H,N—CH$_3$), 9.69(s,1H,—CHO); MS, m/z: 178(M+). Anal. Calcd for C$_9$H$_{10}$N$_2$O$_2$: C, 60.70; H, 5.66; N, 15.72. Found: C, 60.74; H, 5.53; N, 15.62.

EXAMPLE 2-2

2-ethyl-3,4-dimethylfuro[2,3-c]pyrazole (IV-2)

Cupric sulfate (10.0 g) was dissolved in water and zinc powder (3.0 g) was added to the solution stepwise to form precipitate. The precipitate was collected by filtration and washed with 10% HCl solution, then washed with water and dried to obtain the desired active copper.

The compound III-2 (5.0 g, 0.024 mol) was dissolved in dry quinoline (60 ml), and the active copper (1.0 g, 0.016 mol) was added, which was then heated and maintained at 200° C. while stirring. After the reaction was completed, the reaction mixture was cooled to room temperature and acidified with 10% HCl solution, and then filtered. The filtrate was extracted with chloroform, and the chloroform layer was washed with water for several times, dried with anhydrous magnesium sulfate to remove water therefrom, and filtered. The solvent medium was removed from the filtrate by evaporation under reduced pressure, and the residue was purified by column chromatography (silica gel-chloroform) to give compound IV-2 in light yellow crystal form. Yield, 3.2 g (80%).

mp: 32°–34° C.; UV (CHCl$_3$) $\lambda_{max}$: 259 nm; $^1$H-NMR(CDCl$_3$) δ:1.4(t,3H,—CH$_2$CH$_3$), 2.1(s,3H,C-4—CH$_3$), 2.4(s,3H,C-3,—CH$_3$), 4.03(q,2H,—CH$_2$CH$_3$), 6.9(s,1H,C-5—H); MS, m/z:164(M+). Anal. Calcd for C$_9$H$_{12}$N$_2$O: C, 65.83; H, 7.37, N, 17.06. Found: C, 65.80; H, 7.34; N, 17.17.

2-ethyl-3,4-dimethylfuro[2,3-c]pyrazole-5-carbaldehyde (V-2)

N,N-dimethylformamide, DMF, (30 g, 0.41 mol) was added dropwise and slowly to phosphoryl chloride (10 g, 0.065 mol) at 5°–10° C. while stirring, and the solution was stirred at 10° C. for additional 20 minutes. To the solution, a solution of compound IV-2 (1.0 g, 0.0067 mole) in dimethylformamide (20 ml) was added dropwise and slowly at 0°–5° C. while stirring, and maintained stirring at 0°–5° C. for 30 minutes and at room temperature for additional 30 minutes. The reaction mixture was poured into ice water, which was then neutrized with sodium carbonate and settled at room temperature for a period of time to form crystal. The resulting crystal was collected by filtration and dried to give compound V-2 in light yellow needle crystal form. Yield, 0.80 g (68%).

mp: 93°–94° C.; IR (KBr) $\nu_{max}$: 2720(—CHO), 1680(C=O)cm$^{-1}$; UV(CHCl$_3$) $\lambda_{max}$: 320 nm; $^1$H-NMR(CDCl$_3$) δ:1.43(t,3H,—CH$_2$CH$_3$), 2.53(s,3H,C-4—CH$_3$), 2.57(s,3H,C-3—CH$_3$), 4.13(q,2H,—CH$_2$CH$_3$), 9.65(s,1H,—CHO); MS, m/z: 192(M+). Anal. Calcd for C$_{10}$H$_{12}$N$_2$O$_2$: C, 62.49; H, 6.29; N, 14.57. Found: C, 62.35; H, 6.40; N, 15.63.

Scheme 4

Part three: preparation of 2-,3-,4-trisubstituted-5-acylfuro-[2,3-c]pyrazoles (VI)

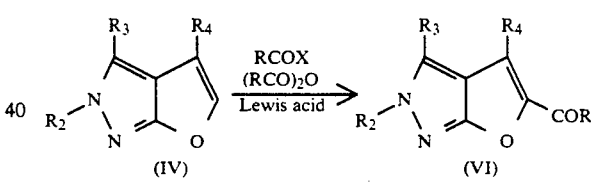

wherein R$_2$, R$_3$ and R$_4$ represent the same meanings as defined above.

Compound IV was dissolved in a suitable solvent (e.g. nitrobenzene) and an acylation reaction was conducted in the presence of Lewis acid (e.g. 98% H3PO4). The product was purified by column chromatography and recrystalization to give the desired compound VI.

EXAMPLE 3-1

5-acetyl-2,3,4-trimethylfuro[2,3-c]pyrazole (VI-1)

10 g of a mixture of 98% phosphoric acid and 95% acetic anhydride was prepared.

Compound IV-1 (1.0 g, 0.0067 mol) and acetic anhydride (18.8 g, 0.2 mol) was mixed and heated to 35° C., and then the mixture of phosphoric acid and acetic anhydride prepared above was added dropwise and slowly (the temperature did not exceed 40° C.). After that, the mixture was stirred at 55°–60° C. for 90 minutes, and then cooled to a temperature lower than 20° C., and finally 80 ml of water was added. After 30 minutes, the reaction mixture was extracted with chloroform. The chloroform layer was washed with 100 ml water and 10% potassium carbonate solution and water again, and finally dried with anhydrous magnesium sulfate to remove water therefrom, and filtered. The solvent medium was removed from the filtrate by evaporation under reduced pressure, and the residue was purified by column chromatography (silica gel-chloroform) to give compound VI-1 in white needle crystal form. Yield, 0.18 g (14%).

mp: 136°–138° C.; IR (KBr) $v_{max}$: 1655(C=O)cm$^{-1}$; UV(CHCl$_3$) $\lambda_{max}$: 314 nm; $^1$H-NMR(CDCl$_3$) δ:2.43(s,6H,C-3—CH$_3$ or C-4—CH$_3$ or —COCH$_3$), 2.50(s,3H,C-3—CH$_3$ or C-4—CH$_3$ or —COCH$_3$), 3.83(s,3H,N—CH$_3$); MS, m/z: 192(M$^+$), 177(M$^+$—15). Anal. Calcd for C$_{10}$H$_{12}$N$_2$O$_2$: C, 62.49; H, 6.29; N, 14.57. Found: C, 62.54; H, 6.35; N, 14.68.

Scheme 5
Part four: preparation of 2-,3-,4-Trisubstituted furo[2,3-c]pyrazole-5-carboxamide (VIII)

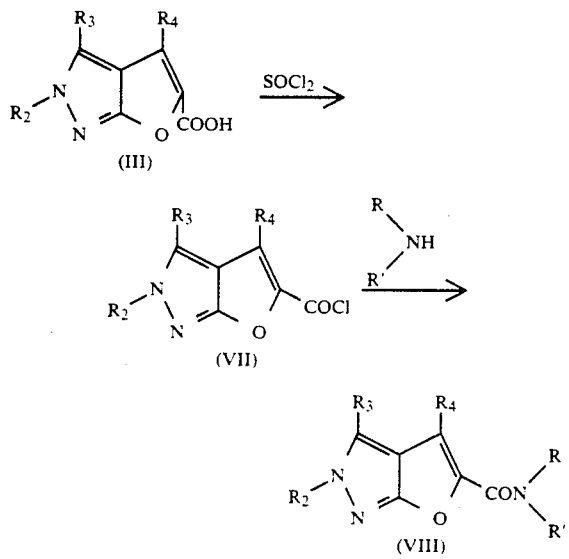

wherein R$_2$, R$_3$ and R$_4$ represent the same meanings as defined above.

Compound III which was dissolved in a suitable solvent (e.g. benzene) was reacted with thionyl chloride to obtain 2,3,4-trisubstituted furo[2,3-c]pyrazole-5-carboxylic acid chloride (VII). The compound VII was then reacted with an amine in a suitable solvent, and the product was purified by column chromatography and recrystalization to give the desired compound VIII.

EXAMPLE 4-1

2,3,4-trimethylfuro[2,3-c]pyrazole-5-acid chloride (VII-1)

Compound III-1 (1.0 g, 0.0052 mol) was suspended in benzene (100 ml) and thionyl chloride (5.0 g, 0.042 mol) was added. The mixture was then heated under reflux until the reaction was completed, and the solvent was evaporated from the reaction mixture. The residue was washed with n-hexane, and recrystallized from petroleum ether-ethyl acetate to give compound VII-1 in white crystal form. Yield, 0.93 g (85%).

2,3,4-trimethylfuro[2,3-c]pyrazole-5-carboxamide (VIII-1)

Compound VII-1 (1.0 g, 0.0047 mol) was dissolved in benzene (40 ml) and ammonia was bubbled into the solution while stirring. After the reaction was completed, the reaction mixture was filtered, and the solid portion was washed with water and dried. The filtrate portion was washed with water and dried over anhydrous magnesium sulfate and filtered, and finally the benzene solvent was evaporated from the filtrate. The residue and the solid portion were combined and purified by column chromatography (silica gel-chloroform) to give compound VIII-1 in white crystal form. Yield, 0.55 g (61%).

mp: 148°–150° C.; IR (KBr) $v_{max}$: 3300, 3120(NH$_2$), 1670(C=O)cm$^{-1}$; UV(CHCl$_3$) $\lambda_{max}$: 288 nm; $^1$H-NMR(CF$_3$COOD) δ:2.66(s,3H,C-3—CH$_3$ or C-4—CH$_3$), 2.73(s,3H,C-3—CH$_3$ or C-4—CH$_3$), 4.17(s,3H,N—CH$_3$); MS, m/z: 193(M$^+$). Anal. Calcd for C$_9$H$_{11}$N$_3$O$_2$: C, 55.95; H, 5.74; N, 21.75. Found: C, 55.83; H, 5.70; N, 21.71.

EXAMPLE 4-2

N-methyl-2,3,4-trimethylfuro[2,3-c]pyrazole-5-carboxamide (VIII-2)

Compound VII-1 (1.0 g, 0.0047 mol) was dissolved in benzene (40 ml) and methylamine was introduced into the solution while stirring. After the reaction was completed, the reaction mixture was washed with water and dried over anhydrous magnesium sulfate and filtered, and finally the benzene solvent was evaporated from the filtrate. The residue was purified by column chromatography (silica gel-chloroform) to give compound VIII-2 in yellow crystal form. Yield, 0.80 g (82%).

mp: 186°–188° C.; IR (KBr) $v_{max}$: 3340(NH), 1630(C=O)cm$^{-1}$; UV(CHCl$_3$) $\lambda_{max}$: 279 nm; $^1$H-NMR(CDCl$_3$) δ:2.40(s,3H, C-3—CH$_3$ or C-4—CH$_3$), 2.50(s,3H,C-3—CH$_3$ or C-4—CH$_3$), 2.93(d,3H,—CONH—CH$_3$), 3.79(s,3H,N—CH$_3$), 6.50(s,1H,NH); MS, m/z: 207(M$^+$). Anal. Calcd for C$_{10}$H$_{13}$N$_3$O$_2$: C, 57.96; H, 6.32; N, 20.28. Found: C, 57.79; H, 6.30; N, 20.28.

EXAMPLE 4-3

N-ethyl-2,3,4-trimethylfuro[2,3-c]pyrazole-5-carboxamide (VIII-3)

Compound VII-1 (1.0 g, 0.0047 mol) was dissolved in benzene (40 ml) and ethylamine (2.0 g, 0.044 mol) was introduced into the solution while stirring. After the reaction was completed, the reaction mixture was washed with water and dried over anhydrous magnesium sulfate and filtered, and finally the benzene solvent was evaporated from the filtrate. The residue was purified by column chromatography (silica gel-chloroform) to give compound VIII-3 in yellow crystal form. Yield, 0.98 g (94%).

mp: 172°–174° C.; IR (KBr) $v_{max}$: 3360(NH), 1630(C=O)cm$^{-1}$; UV(CHCl$_3$) $\lambda_{max}$: 285 nm; $^1$H-NMR(CDCl$_3$) δ:1.40(t,3H, —CH$_2$CH$_3$), 2.43(s,3H,C-3—CH$_3$or C-4—CH$_3$), 2.53(s,3H, C-3—CH$_3$ or C-4—CH$_3$), 3.43(m,2H,NHCH$_2$CH$_3$), 3.80(s,3H,N—CH$_3$), 6.57(s,1H,NH); MS, m/z: 221(M$^+$), 177(M$^+$—44). Anal. Calcd for C$_{11}$H$_{15}$N$_3$O$_2$: C, 59.71; H, 6.83; N, 18.99. Found: C, 59.79; H, 6.69; N, 18.87.

EXAMPLE 4-4

N-isopropyl-2,3,4-trimethylfuro[2,3-c]pyrazole-5-carboxamide (VIII-4)

The synthesis and purification procedures for preparing compound VIII-1 as described in Example 4-1 were repeated to obtain compound VIII-4 except that isopropylamine (2 g, 0.033 mol) was used instead of ammonia. Compound VIII-4 obtained is in yellow crystal form. Yield, 1.0 g (98%).

mp: 168°-170° C.; IR (KBr) $v_{max}$: 3400(NH), 1630(C=O)cm$^{-1}$; UV(CHCl$_3$) $\lambda_{max}$: 280 nm; $^1$H-NMR(CDC3l) δ: 1.27(d, 6H, —CH(CH$_3$)$_2$), 2.47(s,3H, C-3—CH$_3$ or C-4—CH$_3$), 2.50(s, 3H, C-3—CH$_3$ or C-4—CH$_3$), 3.83(s,3H,N—CH$_3$), 4.17(m, 1H,—CH(CH$_3$)$_2$), 6.20(s,1H,NH); MS, m/z: 235(M$^+$), 177(M$^+$—58). Anal. Calcd for C$_{12}$H$_{17}$N$_3$O$_2$: C, 61.26; H, 7.28, N, 17.86. Found: C, 61.30; H, 7.35; N, 17.69.

EXAMPLE 4-5

N-isoamyl-2,3,4-trimethylfuro[2,3-c]pyrazole-5-carboxamide (VIII-5)

The synthesis and purification procedures for preparing compound VIII-1 as described in Example 4-1 were repeated to obtain compound VIII-5 except that isoamylamine (3 g, 0.034 mol) was used instead of ammonia. Compound VIII-5 obtained is in yellow crystal form. Yield, 1.2 g (97%).

mp: 146°-148° C.; IR (KBr) $v_{max}$: 3330(NH), 1630(C=O)cm$^{-1}$; UV(CHCl$_3$) $\lambda_{max}$: 285 nm; $^1$H-NMR(CDCl$_3$) δ:0.93(d,6H, —CH(CH$_3$)$_2$), 1.33-2.00(m,3H, —CH$_2$—CH(CH$_3$)$_2$), 2.43(s, 3H,C-3—CH$_3$ or C-4—CH$_3$), 2.53(s,3H,C-3—CH$_3$ or C-4—CH$_3$), 3.37(m,2H,—NHCH$_2$CH$_2$—), 3.77(s,2H,N—CH$_2$—), 6.40(s,1H,NH); MS, m/z: 263(M$^+$), 177(M$^+$—86). Anal. Calcd for C$_{14}$H$_{21}$N$_3$O$_2$: C, 63.85; H, 8.04; N, 15.96. Found: C, 63.77; H, 8.14; N, 15.87.

EXAMPLE 4-6

N-cyclohexyl-2,3,4-trimethylfuro[2,3-c]pyrazole-5-carboxamide (VIII-6)

The synthesis and purification procedures for preparing compound VIII-1 as described in Example 4-1 were repeated to obtain compound VIII-6 except that cyclohexylamine (3 g, 0.0047 mol) was used instead of ammonia. Compound VIII-6 obtained is in dark red crystal form. Yield, 0.15 g (62%).

mp: 138°-140° C.; IR (KBr) $v_{max}$: 3350(NH), 1630(C=O)cm$^{-1}$; UV(CHCl$_3$) $\lambda_{max}$: 280 nm; $^1$H-NMR(CDCl$_3$) δ:0.73-2.10 (m,11H,cyclohexyl protons), 2.30(s,3H,C-3—CH$_3$ or C-4—CH$_3$), 2.40(s,3H,C-3—CH$_3$ or C-4—CH$_3$), 3.70(s,3H,N—CH$_3$), 6.17(s,1H,NH); MS, m/z: 275(M$^+$), 177(M$^+$-98). Anal. Calcd for C$_{15}$H$_{21}$N$_3$O$_2$: C, 65.43, H:7.69; N, 15.26. Found: C, 65.49; H, 7.61; N, 15.32.

EXAMPLE 4-7

N-(N',N'-dimethylaminopropylamino)-2,3,4-trimethylfuro[2,3-c]pyrazole-5-carboxamide (VIII-7)

The synthesis and purification procedures for preparing compound VIII-1 as described in Example 4-1 were repeated to obtain compound VIII-7 except that N,N-dimethyltrimethylenediamine (4 g, 0.040 mol) was used instead of ammonia. Compound VIII-7 obtained is in yellow crystal form. Yield, 0.6 g (58%).

mp: 235°-238° C.; IR (KBr) $v_{max}$: 3410(NH), 1630(C=O)cm$^{-1}$; UV(CHCl$_3$) $\lambda_{max}$: 286 nm; $^1$H-NMR(CDCl$_3$) δ: 1.67 (m,2H,NH—CH$_2$CH$_2$CH$_2$—), 2.20(s,6H,N(CH$_3$)$_2$), 2.33(s,3H, C-3—CH$_3$ or C-4—CH$_3$), 2.50(s,3H,C-3—CH$_3$ or C-4—CH$_3$), 3.30(t,2H,—CH$_2$CH$_2$N<), 3.43(m,2H,NHCH$_2$), 3.80(s,3H,N—CH$_3$), 7.67(s,1H,NH); MS, m/z: 278(M$^+$), 177(M$^+$-101). Anal. Calcd for C$_{14}$H$_{22}$N$_4$O$_2$: C, 60.41; H, 7.97; N, 20.13. Found: C, 60.40; H, 7.89; N, 20.23.

EXAMPLE 4-8

N-(p-ethoxycarbonylmethylenephenyl)-2,3,4-trimethylfuro[2,3-c]pyrazole-5-carboxamide (VIII-8)

The synthesis and purification procedures for preparing compound VIII-1 as described in Example 4-1 were repeated to obtain compound VIII-8 except that ethyl 1-(4-aminophenyl) acetate (2.83 g, 0.016 mol) was used instead of ammonia and 1.7 g (0.008 mol) compound VII-1 was used. Compound VIII-8 obtained is in yellow crystal form. Yield, 1.1 g (66%).

mp: 213°-215° C.; IR (KBr) $v_{max}$: 3300(NH), 1730(C=O), 1660(C=O)cm$^{-1}$; UV(CHCl$_3$) $\lambda_{max}$: 305 nm; $^1$H-NMR(CDCl$_3$) δ: 1.23(t,3H,—CHC$_2$H$_3$), 2.43(s,3H,C-3—CH$_3$ or C-4—CH$_3$), 2.60(s,3H,C-3—CH$_3$ or C-4—CH$_3$), 3.57(s,2H,C$_6$H$_5$—CH$_2$—CO—), 3.80(s,3H,N—CH$_3$), 4.13(q,2H,OCH$_2$CH$_3$), 7.23(d,2H,J=8 Hz,3'& 5'—H), 7.60(d,2H, J=8 Hz,2'& 6'—H), 8.13(s,1H,NH); MS, m/z: 355(M$^+$). Anal. Calcd for C$_{19}$H$_{21}$N$_3$O$_4$: C, 64.21; H, 5.96; N, 11.82. Found: C, 64.30, H:5.84; N, 11.70.

EXAMPLE 4-9

N,N-dimethyl-2,3,4-trimethylfuro[2,3-c]pyrazole-5-carboxamide (VIII-9)

The synthesis and purification procedures for preparing compound VIII-1 as described in Example 4-1 were repeated to obtain compound VIII-9 except that dimethylamine (2 g, 0.044 mol) was used instead of ammonia. Compound VIII-9 obtained is in yellow crystal form. Yield, 0.94 g (89%).

mp: 116°-118° C.; IR (KBr) $v_{max}$: 1610(C=O)cm$^{-1}$; UV(CHCl$_3$) $\lambda_{max}$: 285 nm; $^1$H-NMR(CDCl$_3$) δ: 2.43(s,3H,C-3—CH$_3$ or C-4—CH$_3$), 2.46(s,3H,C-3—CH$_3$ or C-4—CH$_3$), 3.17(s,6H,N(CH$_3$)$_2$), 3.80(s,3H,N —CH$_3$); MS, m/z: 221(M$^+$), 177(M$^+$—44). Anal. Calcd for C$_{11}$H$_{15}$N$_3$O$_2$: C, 59.71; H, 6.83; N, 18.99. Found: C, 59.60; H, 6.71; N, 18.75.

EXAMPLE 4-10

N,N-diethyl-2,3,4-trimethylfuro[2,3-c]pyrazole-5-carboxamide (VIII-10)

The synthesis and purification procedures for preparing compound VIII-1 as described in Example 4-1 were repeated to obtain compound VIII-10 except that diethylamine (2 g, 0.027 mol) was used instead of ammonia. Compound VIII-10 obtained is in yellow crystal form. Yield, 0.19 g (81%).

mp: 152°-154° C.; IR (KBr) $v_{max}$:1605(C=O)cm$^{-1}$; UV(CHCl$_3$) $\lambda_{max}$: 285 nm; $^1$H-NMR(CDCl$_3$) δ: 1.16(m,6H,N (CH$_2$CH$_3$)$_2$), 2.33(s,6H,C-3—CH$_3$ & C-4—CH$_3$), 3.37(m,4H,N(CH$_2$CH$_3$)$_2$), 3.70(s,3H,N—CH$_3$); MS, m/z: 249(M$^+$), 177(M$^+$—72). Anal. Calcd for C$_{13}$H$_{19}$N$_3$O$_2$: C, 62.63; H, 7.68, N, 16.85. Found: C, 62.71; H, 7.60; N, 16.81.

EXAMPLE 4-11

5-(N-piperidinylcarbonyl)-2,3,4-trimethylfuro[2,3-c]pyrazole (VIII-11)

The synthesis and purification procedures for preparing compound VIII-1 as described in Example 4-1 were repeated to obtain compound VIII-11 except that piperidine (3 g, 0.034 mol) was used instead of ammonia.

Compound VIII-11 obtained is in white crystal form. Yield, 1.05 g (85%).

mp: 156°-158° C.; IR (KBr) $\nu_{max}$: 1610(C=O)cm$^{-1}$; UV(CHCl$_3$) $\lambda_{max}$: 280 nm; $^1$H-NMR(CDCl$_3$) δ: 1.67

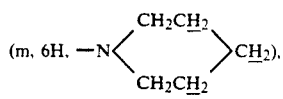

2.37(s,6H,C-3—CH$_3$ & C-4—CH$_3$), 3.57

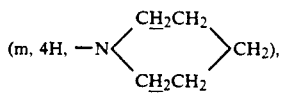

3.80(s,3H,N—CH$_3$); MS, m/z: 261(M$^+$), 177(M$^+$—84), 150(M$^+$—111). Anal. Calcd for C$_{14}$H$_{19}$N$_3$O$_2$: C, 64.35; H, 7.33; N, 16.08. Found: C, 64.22; H, 7.30; N, 16.12.

EXAMPLE 4-12

5-(N-morpholinylcarbonyl)-2,3,4-trimethylfuro[2,3-c]pyrazole (VIII-12)

The synthesis and purification procedures for preparing compound VIII-1 as described in Example 4-1 were repeated to obtain compound VIII-12 except that morpholine (3 g, 0.030 mol) was used instead of ammonia. Compound VIII-12 obtained is in white crystal form. Yield, 1.1 g (89%).

mp: 183°-185° C.; IR(KBr) $\nu_{max}$: 1610(C=O)cm$^{-1}$; UV(CHCl$_3$) $\lambda_{max}$: 280 nm; $^1$H-NMR(CDCl$_3$) δ: 2.37(s,3H,C-3—CH$_3$ or C-4—CH$_3$), 2.39(s,3H,C-3—CH$_3$ or C-4—CH$_3$), 3.67

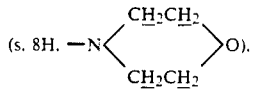

3.76(s,3H,N—CH$_3$); MS, m/z: 263 (M$^+$), 177(M$^+$—86). Anal. Calcd for C$_{13}$H$_{17}$N$_3$O$_3$: C, 59.30; H, 6.51; N, 15.96. Found: C, 59.20; H, 6.39, N:15.81.

EXAMPLE 4-13

N-(N'-methylpiperazinyl)-2,3,4-trimethyl-furo[2,3-c]pyrazole-5-carboxamide (VIII-13)

The synthesis and purification procedures for preparing compound VIII-1 as described in Example 4-1 were repeated to obtain compound VIII-13 except that N-methylpiperazine (3 g, 0.030 mol) was used instead of ammonia. Compound VIII-13 obtained is in yellow crystal form. Yield, 1.2 g (92%).

mp: 145°-147° C.; IR (KBr) $\nu_{max}$: 1615(C=O)cm$^{-1}$; UV(CHCl$_3$)$\lambda_{max}$: 288 nm; $^1$H-NMR(CDCl$_3$) δ: 2.33(s,3H, —N—N—CH$_3$), 2.40(s,6H,C-3—CH$_3$ & C-4—CH$_3$),

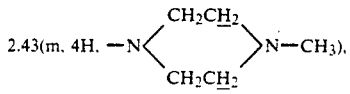

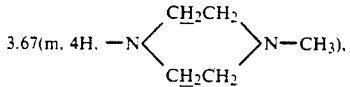

3.83(s,3H,N—CH$_3$); MS, m/z: 276(M$^+$), 177(M$^+$-99), 99(M$^+$-177). Anal. Calcd for C$_{14}$H$_{20}$N$_4$O$_2$: C, 60.85; H, 7.29, N, 20.27. Found: C, 60.74; H, 7.32; N, 20.35.

EXAMPLE 4-14

N-propyl-2,3,4-trimethylfuro[2,3-c]pyrazole-5-carboxamide (VIII-14)

The synthesis and purification procedures for preparing compound VIII-1 as described in Example 4-1 were repeated to obtain compound VIII-14 except that propylamine (0.61 g, 0.011 mol) was used instead of ammonia. Compound VIII-14 obtained is in yellow crystal form. Yield, 0.7 g (63%).

mp: 113°-115° C.; IR (KBr) $\nu_{max}$: 3270(NH), 1630(C=O)cm$^{-1}$; UV(CHCl$_3$) $\lambda_{max}$: 275 nm; $^1$H-NMR(CDCl$_3$) δ: 0.94(t,3H, NH(CH$_2$)$_2$CH$_3$), 1.53(m,2H,—NHCH$_2$CH$_2$CH$_3$), 2.37(s,3H,C-4—CH$_3$), 2.49(s,3H,C-3—CH$_3$), 3.33(m,2H,—NHCH$_2$CH$_2$CH$_3$), 3.76(s,3H,N—CH$_3$), 6.23-6.63(br,1H,—NH—); MS, m/z: 235(M$^+$). Anal. Calcd for C$_{12}$H$_{17}$N$_3$O$_2$: C, 61.26; H, 7.28, N, 17.86. Found: C, 61.35; H, 7.31; N, 17.69.

EXAMPLE 4-15

N-butyl-2,3,4-trimethylfuro[2,3-c]pyrazole-5-carboxamide (VIII-15)

The synthesis and purification procedures for preparing compound VIII-1 as described in Example 4-1 were repeated to obtain compound VIII-15 except that butylamine (0.75 g, 0.011 mol) was used instead of ammonia. Compound VIII-15 obtained is in yellow and white crystal form. Yield, 1.0 g (85%).

mp: 109°-110° C.; IR (KBr) $\nu_{max}$: 3300(NH), 1630(C=O)cm$^{-1}$; UV(CHCl$_3$) $\lambda_{max}$: 284 nm; $^1$H-NMR(CDCl$_3$) δ: 0.93(t,3H, —NH(CH$_2$)$_3$CH$_3$), 1.20-1.71(m,4H,—NHCH$_2$CH$_2$CH$_2$CH$_3$), 2.40 (s,3H,C-4—CH$_3$), 2.53(s,3H,C-3—CH$_3$), 3.20-3.60(m,2H, —NHCH$_2$CH$_2$CH$_2$CH$_3$), 3.78(s,3H,N—CH$_3$), 6.20-6.57(br,1H, —NH—); MS, m/z: 249(M$^+$). Anal. Calcd for C$_{13}$H$_{19}$N$_3$O$_2$: C, 62.63; H, 7.68; N, 16.85. Found: C, 62.60; H, 7.64; N, 16.83.

EXAMPLE 4-16

N-pentyl-2,3,4-trimethylfuro[2,3-c]pyrazole-5-carboxamide (VIII-16)

The synthesis and purification procedures for preparing compound VIII-1 as described in Example 4-1 were repeated to obtain compound VIII-16 except that pentylamine (0.96 g, 0.011 mol) was used instead of ammonia. Compound VIII-16 obtained is in light yellow crystal form. Yield, 0.90 g (73%).

mp: 106°-107° C.; IR (KBr) $\nu_{max}$: 3360(NH), 1630(C=O)cm$^{-1}$; UV(CHCl$_3$) $\lambda_{max}$: 285 nm; $^1$H-NMR(CDCl$_3$) δ: 0.65-1.05 (m,3H,—NH(CH$_2$)$_4$—CH$_3$), 1.08-1.72(m,6H,—NHCH$_2$CH$_2$CH$_2$CH$_2$CH$_3$), 2.37(s,3H,C-4—CH$_3$), 2.49(s,3H,C-3—CH$_3$), 3.30-3.52(m,2H,—NHCH$_2$—(CH$_2$)$_3$CH$_3$), 3.74(s,3H,N—CH$_3$), 6.15-6.52(br,1H,—NH—); MS, m/z: 263(M$^+$). Anal. Calcd for C$_{14}$H$_{21}$N$_3$O$_2$: C, 63.85; H, 8.04; N, 15.96. Found: C, 63.91; H, 8.12; N, 15.84.

EXAMPLE 4-17

2-ethyl-3,4-dimethylfuro[2,3-c]pyrazole-5-carboxylic acid chloride (VII-2)

Compound III-2 (1.0 g, 0.0048 mol) was suspended in anhydrous benzene (100 ml) and thionyl chloride (4.6 g, 0.039 mol) was added. The mixture was then heated under reflux until the reaction was completed, and the solvent was evaporated from the reaction mixture. The residue was washed with petroleum ether and dried to give compound VII-2 in yellow brown crystal form. Yield, 1.0 g (92%).

2-ethyl-3,4-trimethylfuro[2,3-c]pyrazole-5-carboxamide (VIII-17)

Compound VII-2 (1.0 g, 0.0044 mol) was dissolved in benzene (100 ml) and ammonia was bubbled into the solution while heating under reflux. After the reaction was completed, the reaction mixture was filtered, and the solid portion was washed with water and dried. The filtrate portion was washed with water and dried over anhydrous magnesium sulfate and filtered, and finally the benzene solvent was evaporated from the filtrate. The residue and the solid portion were combined and purified by column chromatography (silica gel-chloroform) to give compound VIII-17 in light yellow crystal form. Yield, 0.65 g (71%).

mp: 265°–267° C.; IR (KBr) $\nu_{max}$: 3300, 3150NH$_2$), 1680 (C=O)cm$^{-1}$; UV(C$_2$H$_5$OH) $\lambda_{max}$: 283 nm; $^1$H-NMR(DMSO—d$_6$) δ: 1.14(t,3H,N—CH$_2$CH$_3$), 2.37(s,6H,C-4—CH$_3$ & C-3—CH$_3$), 3.98(q,2H,—CH$_2$CH$_3$), 6.97–7.42(br,2H,—NH$_2$); MS, m/z: 207(M$^+$). Anal. Calcd for C$_{10}$H$_{13}$N$_3$O$_2$: C, 57.96; H, 6.32; N, 20.28. Found: C, 57.79; H, 6.38; N, 20.34.

EXAMPLE 4-18

N-methyl-2-ethyl-3,4-dimethylfuro[2,3-c]pyrazole-5-carboxamide (VIII-18)

Compound VII-2 (1.0 g, 0.0044 mol) was dissolved in benzene (100 ml) and methylamine was introduced into the solution while heating under reflux. After the reaction was completed, the reaction mixture was washed with water, and then the benzene layer was dried over anhydrous magnesium sulfate and filtered, and finally the benzene solvent was evaporated from the filtrate. The residue was purified by column chromatography (silica gel-chloroform) to give compound VIII-18 in light yellow crystal form. Yield, 0.85 g (87%).

mp: 171°–172° C.; IR (KBr) $\nu_{max}$:3340(NH), 1640(C=O)cm$^{-1}$; UV(CHCl$_3$) $\lambda_{max}$: 277 nm; $^1$H-NMR(CDCl$_3$) δ: 1.41(t,3H, —CH$_2$CH$_3$), 2.43(s,3H,C-4—CH$_3$), 2.55(s,3H,C-3—CH$_3$), 2.94(d,3H,—NHCH$_3$), 4.09(q,2H,—CH$_2$CH$_3$), 6.16–6.57(br, 1H,—NHCH$_3$); MS, m/z: 221(M$^+$). Anal. Calcd for C$_{11}$H$_{15}$N$_3$O$_2$: C, 59.71; H, 6.83; N, 18.99. Found: C, 59.65, H, 6.80; N, 18.95.

EXAMPLE 4-19

N-ethyl-2-ethyl-3,4-dimethylfuro[2,3-c]pyrazole-5-carboxamide (VIII-19)

Compound VII-2 (1.0 g, 0.0044 mol) was dissolved in benzene (100 ml) and ethylamine was introduced into the solution while heating under reflux. After the reaction was completed, the reaction mixture was washed with water, and then the benzene layer was dried over anhydrous magnesium sulfate and filtered, and finally the benzene solvent was evaporated from the filtrate. The residue was purified by column chromatography (silica gel-chloroform) to give compound VIII-19 in light yellow crystal form. Yield, 0.60 g (58%).

mp: 129°–131° C.; IR (KBr) $\nu_{max}$: 3360(NH), 1640(C=O)cm$^{-1}$; UV(CHCl$_3$) $\lambda_{max}$: 281 nm; $^1$H-NMR(CDCl$_3$) δ: 1.03–1.53 (m,6H,N—N—CH$_2$—CH$_3$ & —CONHCH$_2$CH$_3$), 2.43(s,3H,C-4—CH$_3$),2.55(s,3H,C-3—CH$_3$), 3.13–3.70(m,2-H,—CONHCH$_2$ CH$_3$), 4.07(q,2H,N—N—CH$_2$CH$_3$), 5.97–6.53(br,1H,—NH); MS, m/z: 235(M$^+$). Anal. Calcd for C$_{12}$H$_{17}$N$_3$O$_2$: C, 61.26, H, 7.28; N, 17.86. Found: C, 61.32; H, 7.32; N, 17.75.

EXAMPLE 4-20

N-propyl-2-ethyl-3,4-dimethylfuro[2,3-c]pyrazole-5-carboxamide (VIII-20)

Compound VII-2 (1.0 g, 0.0044 mol) was dissolved in benzene (100 ml) and propylamine (0.6 g, 0.0097) was introduced into the solution while heating under reflux. After the reaction was completed, the reaction mixture was washed with water, and then the benzene layer was dried over anhydrous magnesium sulfate and filtered, and finally the benzene solvent was evaporated from the filtrate. The residue was purified by column chromatography (silica gel-chloroform) to give compound VIII-20 in light yellow crystal form. Yield, 0.65 g (59%).

mp: 113°–115° C.; IR (KBr) $\nu_{max}$: 3360(NH), 1640(C=O)cm$^{-1}$; UV(CHCl$_3$) $\lambda_{max}$: 275 nm; $^1$H-NMR(CDCl$_3$) δ: 0.96(t,3H, —N(CH$_2$)$_2$CH$_3$), 1.42(t,3H,—NCH$_2$CH$_3$), 1.55(m,2H,N—CH$_2$ CH$_2$CH$_3$), 2.43(s,3H, C-4—CH$_3$), 2.55(s,3H, C-3—CH$_3$), 3.13–3.61(m,2H,NCH$_2$CH$_2$CH$_3$), 3.85–4.37(m,2H, N—CH$_2$CH$_3$), 6.31–6.57(br,1H,—NH); MS, m/z: 249(M$^+$). Anal. Calcd for C$_{13}$H$_{19}$N$_3$O$_2$,: C, 62.63; H, 7.68; N, 16.85. Found: C, 62.70; H, 7.72; N, 16.85.

EXAMPLE 4-21

N-butyl-2-ethyl-3,4-dimethylfuro[2,3-c]pyrazole-5-carboxamide (VIII-21)

Compound VII-2 (1.0 g, 0.0044 mol) was dissolved in benzene (100 ml) and butylamine (0.8 g, 0.0097) was introduced into the solution while heating under reflux. After the reaction was completed, the reaction mixture was washed with water, and then the benzene layer was dried over anhydrous magnesium sulfate and filtered, and finally the benzene solvent was evaporated from the filtrate. The residue was purified by column chromatography (silica gel-chloroform) to give compound VIII-21 in light yellow crystal form. Yield, 0.64 g (56%).

mp: 79°–80° C.; IR (KBr) $\nu_{max}$: 3370(NH), 1640(C=O)cm$^{-1}$; UV(CHCl$_3$) $\lambda_{max}$: 286 nm; $^1$H-NMR(CDCl$_3$) δ: 0.93(m,3H,—N (CH$_2$)$_3$CH$_3$), 1.17–1.60(m,7H,N—CH$_2$CH$_2$CH$_2$CH$_3$ & N—CH$_2$ CH$_3$), 2.45(s,3H,C-4—CH$_3$), 2.53(s,3H,C-3—CH$_3$), 3.17–3.52(m,2H,NCH$_2$CH$_2$CH$_2$CH$_3$), 4.10(q,2H,N—CH$_2$CH$_3$), 6.13–6.60(br,1H,—NH—); MS, m/z: 263(M$^+$). Anal. Calcd for C$_{14}$H$_{21}$N$_3$O$_2$: C, 63.85; H, 8.04; N, 15.96. Found: C, 63.80; H, 8.16; N, 15.92.

EXAMPLE 4-22

N-isopropyl-2-ethyl-3,4-dimethylfuro[2,3-c]pyrazole-5-carboxamide (VIII-22)

The synthesis and purification procedures for preparing compound VIII-1 as described in Example 4-1 were repeated to obtain compound VIII-22 except that isopropylamine (0.6 g, 0.0097 mol) was used instead of ammonia and compound VII-2 (1.0 g, 0.0044 mol) was used instead of compound VIII-1. Compound VIII-22 obtained is in light yellow crystal form. Yield, 0.75 g (68%).

mp: 110°–113° C.; IR (KBr) ν$_{max}$: 3400(NH), 1630(C=O)cm$^{-1}$; UV(CHCl$_3$) λ$_{max}$: 286 nm; $^1$H-NMR(CDCl$_3$) δ: 0.58–1.72 (m,10H,—N—CH—(CH$_3$)$_2$ & N—CH$_2$CH$_3$), 2.44(s,3H,C-4—CH$_3$), 2.57(s,3H,C-3—CH$_3$), 4.11(q,2H,N—CH$_2$CH$_3$); MS, m/z: 249(M$^+$). Anal. Calcd for C$_{13}$H$_{19}$N$_3$O$_2$: C, 62.63; H, 7.68, N, 16.85. Found: C, 62.59; H, 7.60; N, 16.74.

EXAMPLE 4-23

N,N-diethyl-2-ethyl-3,4-dimethylfuro[2,3-c]pyrazole-5-carboxamide (VIII-23)

The synthesis and purification procedures for preparing compound VIII-1 as described in Example 4-1 were repeated to obtain compound VIII-23 except that diethylamine (0.7 g, 0.0097 mol) was used instead of ammonia and compound VII-2 (1.0 g, 0.0044 mol) was used instead of compound VII-1. Compound VIII-23 obtained is in light brown crystal form. Yield, 0.55 g (47%).

mp: 63°–65° C.; IR (KBr) ν$_{max}$: 1610(C=O) cm$^{-1}$; UV(CHCl$_3$) λ$_{max}$: 275 nm; $^1$H-NMR(CDCl$_3$) δ: 0.91–1.72

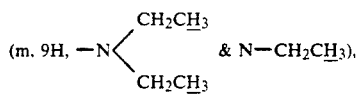

2.43(s,6H,C-4—CH$_3$ & C-3—CH$_3$),

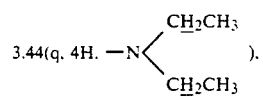

4.06(q,2H,N—CH$_2$CH$_3$); MS, m/z: 263(M$^+$). Anal. Calcd for C$_{14}$H$_{21}$N$_3$O$_2$: C, 63.85; H, 8.04; N, 15.96. Found: C, 63.88; H, 8.15; N, 15.92.

EXAMPLE 4-24

N-benzyl-2-ethyl-3,4-dimethylfuro[2,3-c]pyrazole-5-carboxamide (VIII-24)

The synthesis and purification procedures for preparing compound VIII-1 as described in Example 4-1 were repeated to obtain compound VIII-24 except that benzylamine (1.03 g, 0.0097 mol) was used instead of ammonia and compound VII-2 (1.0 g, 0.0044 mol) was used instead of compound VII-1. Compound VIII-24 obtained is in light brown crystal form. Yield, 0.60 g (46%).

mp: 133°–135° C.; IR (KBr) ν$_{max}$: 3480(NH), 1640(C=O)cm$^{-1}$; UV(CHCl$_3$) λ$_{max}$: 280 nm; $^1$H-NMR(CDCl$_3$) δ: 1.40(t,3H, N—CH$_2$CH$_3$), 2.43(s,3H,C-4—CH$_3$), 2.57(s,3H,C-3—CH$_3$), 3.90–4.23(m,2H,—N—CH$_2$—C$_6$H$_5$), 4.57(q,2H,N—CH$_2$CH$_3$), 7.30(m,5H,—CH$_2$—C$_6$H$_5$); MS, m/z: 297(M$^+$). Anal. Calcd for C$_{17}$H$_{19}$N$_3$O$_2$: C, 68.67; H, 6.44; N, 14.13. Found: C, 68.74; H, 6.49; N, 14.00.

EXAMPLE 4-25

N-[2-(N',N'-dimethylamino)ethyl]-2-ethyl-3,4-dimethylfuro[2,3-c]pyrazole-5-carboxamide (VIII-25)

The synthesis and purification procedures for preparing compound VIII-1 as described in Example 4-1 were repeated to obtain compound VIII-25 except that N,N-dimethylethylamine (0.85 g, 0.0097 mol) was used instead of ammonia and compound VII-2 (1.0 g, 0.0044 mol) was used instead of compound VII-1. Compound VIII-25 obtained is in light yellow crystal form. Yield, 0.95 g (77%).

mp: 55°–56° C.; IR (KBr) ν$_{max}$: 3340(NH), 1635(C=O)cm$^{-1}$; UV(CHCl$_3$) λ$_{max}$: 276 nm; $^1$H-NMR(CDCl$_3$) δ: 1.42(t,3H,N—CH$_2$CH$_3$), 2.20–2.73(m,14H,C-4—CH$_3$ & C-3—CH$_3$ & —CH$_2$CH$_2$N(CH$_3$)$_2$), 3.47(m,2H,—N—CH$_2$—CH$_2$N<), 4.07(q,2H,N—CH$_2$CH$_3$); MS, m/z: 278(M$^+$). Anal. Calcd for C$_{14}$H$_{22}$N$_4$O$_2$: C, 60.41; H, 7.97; N, 20.13. Found: C, 60.43; H, 7.97; N, 20.20.

EXAMPLE 4-26

N-(3,3-diphenylpropyl)-2-ethyl-3,4-dimethylfuro[2,3-c]pyrazole-5-carboxamide (VIII-26)

The synthesis and purification procedures for preparing compound VIII-1 as described in Example 4-1 were repeated to obtain compound VIII-26 except that 3-diphenyl propylamine (2.1 g, 0.0097 mol) was used instead of ammonia and compound VII-2 (1.0 g, 0.0044 mol) was used instead of compound VII-1. Compound VIII-26 obtained is in light yellow crystal form. Yield, 1.40 g (76%).

mp: 134°–135° C.; IR (KBr) ν$_{max}$: 3395(NH), 1630(C=O)cm$^{-1}$; UV(CHCl$_3$) λ$_{max}$: 286 nm; $^1$H-NMR(CDCl$_3$) δ: 1.37(t,3H, N—CH$_2$CH$_3$), 2.25(m,1H,—CH(C$_6$H$_5$)$_2$), 2.38(s,3H,C-4—CH$_3$), 2.51(s,3H,C-3—CH$_3$), 3.32(m,2H,—NCH$_2$CH$_2$CH<), 3.81–4.23(m,4H,—N—CH$_2$—CH$_2$—CH<,-N—CH$_2$CH$_3$), 6.17–6.53(br, 1H,—NH—), 7.23(m,10H,2 ArH); MS, m/z: 401(M$^+$). Anal. Calcd for C$_{25}$H$_{27}$N$_3$O$_2$: C, 74.79; H, 6.78; N, 10.47. Found: C, 74.84; H, 6.69; N, 10.52.

EXAMPLE 4-27

5-(4-phenylpiperazinylcarbonyl)-2-ethyl-3,4-dimethylfuro[2,3-c]pyrazole (VIII-27)

The synthesis and purification procedures for preparing compound VIII-1 as described in Example 4-1 were repeated to obtain compound VIII-27 except that N-phenylpiperazine (1.6 g, 0.0097 mol) was used instead of ammonia and compound VII-2 (1.0 g, 0.0044 mol) was used instead of compound VII-1. Compound VIII-27 obtained is in light yellow crystal form. Yield, 0.85 g (55%).

mp: 128°–130° C.; IR (KBr) νmax: 1625(C=O) cm$^{-1}$; UV (CHCl$_3$) λ$_{max}$: 277 nm; $^1$H-NMR(CDCl$_3$) δ: 1.43(t,3H,N—CH$_2$CH$_3$), 2.43(s,6H,C-4—CH$_3$ & C-3—CH$_3$), 3.06–3.30

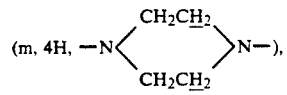

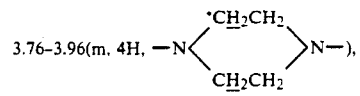

4.06(q,2H,N—CH$_2$CH$_3$), 6.73–7.10(m,5H,ArH); MS, m/z: 352(M$^+$). Anal. Calcd for C$_{20}$H$_{24}$N$_4$O$_2$: C, 68.16; H, 6.86, N, 15.90. Found: C, 68.20; H, 6.91; N, 15.86.

EXAMPLE 4-28

5-[4-(2-pyridyl)piperazinylcarbonyl]-2-ethyl-3,4-dimethylfuro[2,3-c]pyrazole (VIII-28)

The synthesis and purification procedures for preparing compound VIII-1 as described in Example 4-1 were repeated to obtain compound VIII-28 except that 1-(pyridyl)piperazine (1.6 g, 0.0097 mol) was used instead of ammonia and compound VII-2 (1.0 g, 0.0044 mol) was used instead of compound VII-1. Compound VIII-28 obtained is in light yellow crystal form. Yield, 0.95 g (61%).

mp: 129°-131° C.; IR (KBr) $\nu_{max}$: 1618(C=O) cm$^{-1}$; UV(CHCl$_3$) $\lambda_{max}$: 280 nm; $^1$H-NMR(CDCl$_3$) δ: 1.43(t,3H,N—CH$_2$CH$_3$), 2.45(s,6H, C-4—CH$_3$ & C-3—CH$_3$), 3.60-4.01

(m, 8H, 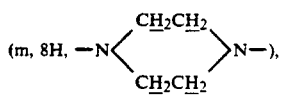 ), 4.10(q,2H,—N—CH$_2$CH$_3$), 6.60-6.73 (m,2H,3',5'—H), 7.27-7.60(m,1H,4'—H); 8.01-8.20(m,1H, 6'—H); MS, m/z: 353(M$^+$). Anal. Calcd for C$_{19}$H$_{23}$N$_5$O$_2$: C, 64.57; H, 6.56; N, 19.82. Found: C, 64.49; H, 6.46, N:19.75.

EXAMPLE 4-29

N-(ethoxycarbonylamino)-2-ethyl-3,4-dimethylfuro[2,3-c]pyrazole-5-carboxamide (VIII-29)

The synthesis and purification procedures for preparing compound VIII-1 as described in Example 4-1 were repeated to obtain compound VIII-29 except that ethyl carbazate (1.0 g, 0.0097 mol) was used instead of ammonia and compound VII-2 (1.0 g, 0.0044 mol) was used instead of compound VII-1. Compound VIII-29 obtained is in light yellow crystal form. Yield, 0.65 g (50%).

mp: 225°-226° C.; IR (KBr) $\nu_{max}$: 3290, 3230(NH), 1740(—COOC$_2$H$_5$), 1660(—CONHNH—)cm$^{-1}$; UV(CHCl$_3$) $\lambda_{max}$: 280 nm; $^1$H-NMR(CDCl$_3$) δ: 1.36(t,3H,N—CH$_2$CH$_3$), 1.52(t,3H,—COOCH$_2$CH$_3$), 2.46(s,3H,C-4—CH$_3$), 2.55(s,3H, C-3—CH$_3$), 4.19(q,2H,N—CH$_2$CH$_3$), 4.23(q,2H,—COOCH$_2$CH$_3$); MS, m/z: 294 (M$^+$). Anal. Calcd for C$_{13}$H$_{18}$N$_4$O$_4$: C, 53.05; H, 6.16; N, 19.04. Found: C, 53.11; H, 6.10; N, 9.12.

EXAMPLE 4-30

2-isopropyl-3,4-dimethylfuro[2,3-c]pyrazole-5-carboxylic acid chloride (VII-3)

Compound III-3 (1.0 g, 0.0045 mol) was suspended in anhydrous benzene (100 ml) and thionyl chloride (4.6 g, 0.039 mol) was added. The mixture was then heated under reflux until the reaction was completed, and the solvent was evaporated from the reaction mixture. The residue was washed with petroleum ether and dried to give compound VII-3 in white color. Yield, 0.93 g (83%).

mp: 162°-164° C.; IR (KBr) $\nu_{max}$: 1680(C=O) cm$^{-1}$; UV(C$_2$H$_5$OH) $\lambda_{max}$: 313 nm($\epsilon$=1.2×10$^4$); $^1$H-NMR(CDCl$_3$) δ: 1.33(d,6H,—CH(CH$_3$)$_2$), 2.48(s,6H,C-4—CH$_3$ & C-3—CH$_3$), 4.52(m,1H,—CH); MS, m/z: 240(M$^+$Anal. Calcd for C$_{11}$H$_{13}$ClN$_2$O$_2$: C, 54.89; H, 5.44; N, 11.64. Found: C, 54.75; H, 5.40; N, 11.58.

isopropyl-3,4-dimethylfuro[2,3-c]pyrazole-5-carboxamide (VIII-30)

Compound VII-3 (1.0 g, 0.0042 mol) was dissolved in benzene (100 ml) and ammonia was bubbled into the solution while heating under reflux. After the reaction was completed, the reaction mixture was filtered, and the solid portion was washed with water and dried. The filtrate portion was washed with water and dried over anhydrous magnesium sulfate and filtered, and finally the benzene solvent was evaporated from the filtrate. The residue and the solid portion were combined and purified by column chromatography (silica gel-chloroform) to give compound VIII-30 in white crystal form. Yield, 0.70 g (76%).

mp: 176°-177° C.; IR(KBr) $\nu_{max}$: 3370(NH), 1680(C=O)cm$^{-1}$; UV(CHCl$_3$) $\lambda_{max}$:302 nm($\epsilon$=9.4×10$^4$)nm; $^1$H-NMR(CDCl$_3$) δ: 1.52(d,6H,—NCH(CH$_3$)$_2$), 2.47(s,3H,C-3—CH$_3$), 2.54 (s,3H,C-4—CH$_3$), 4.48(m,1H,—CH), 6.20-6.50(br,1-H,—NH); MS, m/z: 221(M$^+$). Anal. Calcd for C$_{11}$H$_{15}$N$_3$O$_2$: C, 59.71; H, 6.83; N, 18.99. Found: C, 59.68; H, 6.91; N, 8.90.

EXAMPLE 4-31

N-methyl-2-isopropyl-3,4-dimethylfuro[2,3-c]pyrazole-5-carboxamide (VIII-31)

The synthesis and purification procedures for preparing compound VIII-1 as described in Example 4-1 were repeated to obtain compound VIII-31 except that methylamine was used instead of ammonia and compound VII-3 (1.0 g, 0.0042 mol) was used instead of compound VII-1. Compound VIII-31 obtained is in light yellow crystal form. Yield, 0.80 g (85%).

mp: 148°-150° C.; IR (KBr) $\nu_{max}$: 3370(NH), 1650(C=O)cm$^{-1}$; UV(CHCl$_3$) $\lambda_{max}$:286 nm($\epsilon$=3.3×10$^4$), $^1$H-NMR(CDCl$_3$) δ: 1.52(d,6H,—NCH(CH$_3$)$_2$), 2.47(s,3H,C-3—CH$_3$), 2.54 (s,3H,C-4—CH$_3$), 2.92(d,3H,NHCH$_3$), 4.48(m,1H,—CH), 6.17-6.52(br,1H,—NH); MS, m/z: 235(M$^+$). Anal. Calcd for C$_{12}$H$_{17}$N$_3$O$_2$: C, 61.26; H, 7.28; N, 17.86. Found: C, 61.31; H, 7.32; N, 17.65.

EXAMPLE 4-32

N-ethyl-2-isopropyl-3,4-dimethylfuro[2,3-c]pyrazole-5-carboxamide (VIII-32)

The synthesis and purification procedures for preparing compound VIII-1 as described in Example 4-1 were repeated to obtain compound VIII-32 except that ethylamine was used instead of ammonia and compound VII-3 (1.0 g, 0.0042 mol) was used instead of compound VII-1. Compound VIII-32 obtained is in white crystal form. Yield, 0.60 g (60%).

mp: 128°-130° C.; IR (KBr) $\nu_{max}$: 3370(NH), 1650(C=O)cm$^{-1}$; UV(CHCl$_3$) $\lambda_{max}$: 287 nm($\epsilon$=5.3×10$^4$); $^1$H-NMR(CDCl$_3$) δ: 1.25(t,3H,CH$_2$CH$_3$), 1.52(d,6H,—NCH(CH$_3$)$_2$), 2.47(s, 3H,C-3—CH$_3$), 2.54(s,3H,C-4—CH$_3$), 3.47(q,2H,CH$_2$CH$_3$), 4.48(m,1H,—CH), 6.20-6.52(br,1-H,—NH); MS, m/z: 249(M$^+$). Anal. Calcd for C$_{13}$H$_{19}$N$_3$O$_2$: C, 62.63; H, 7.68; N, 16.85. Found: C, 62.70; H, 7.72; N, 16.74.

EXAMPLE 4-33

N-propyl-2-isopropyl-3,4-dimethylfuro[2,3-c]pyrazole-5-carboxamide (VIII-33)

The synthesis and purification procedures for preparing compound VIII-1 as described in Example 4-1 were repeated to obtain compound VIII-33 except that propylamine (0.60 g, 0.00097 mol) was used instead of ammonia and compound VII-3 (1.0 g, 0.0042 mol) was used instead of compound VII-1. Compound VIII-33 obtained is in light yellow crystal form. Yield, 0.54 g (58%).

mp: 96°-98° C.; IR (KBr) $\nu_{max}$: 3360(NH), 1650(C=O)cm$^{-1}$; UV(CHCl$_3$) $\lambda_{max}$: 288 nm($\epsilon$=1.9×10$^4$);H-NMR(CDCl$_3$) $\delta$: 0.98(t,3H,CH$_2$CH$_2$CH$_3$), 1.52(d,6H,—NCH(CH$_3$)$_2$), 1.55(m,2H,N—CH$_2$CH$_2$CH$_3$), 2.47(s,3H,C-3—CH$_3$), 2.54(s,3H, C-4—CH$_3$), 3.45(m,2H,N—CH$_2$CH$_2$—CH$_3$), 4.48(m,1H,—CH), 6.33-6.54(br,1H,—NH); MS, m/z: 263(M+). Anal. Calcd for C$_{14}$H$_{21}$N$_3$O$_2$: C, 63.85; H, 8.04; N, 15.96. Found: C, 63.81; H, 8.10; N, 15.90.

EXAMPLE 4-34

N-butyl-2-isopropyl-3,4-dimethylfuro[2,3-c]pyrazole-5-carboxamide (VIII-34)

The synthesis and purification procedures for preparing compound VIII-1 as described in Example 4-1 were repeated to obtain compound VIII-34 except that butylamine (0.80 g, 0.0097 mol) was used instead of ammonia and compound VII-3 (1.0 g, 0.0042 mol) was used instead of compound VII-1. Compound VIII-34 obtained is in light yellow crystal form. Yield, 0.72 g (62%).

mp: 104°-106° C.; IR (KBr) $\nu_{max}$: 3370(NH), 1640(C=O)cm$^{-1}$; UV(C$_2$H$_5$OH) $\lambda_{max}$: 285 nm($\epsilon$=1.9×10$^4$); $^1$H-NMR(CDCl$_3$) $\delta$: 0.93(m,3H,N—(CH$_2$)$_3$CH$_3$), 1.22-1.67(m,4-H,—NCH$_2$CH$_2$CH$_2$CH$_3$), 2.47(s,3H,C-3—CH$_3$), 2.54(s,3H,C-4—CH$_3$), 3.22-3.52 (q,2H,N—CH$_2$CH$_2$CH$_2$—CH$_3$), 4.42(m,1H,—CH), 6.17-1.52 (br,1H,—NH); MS, m/z: 277(M+). Anal. Calcd for C$_{15}$H$_{23}$N$_3$O$_2$: C, 64.96; H, 8.36; N, 15.15. Found: C, 64.85; H, 8.30; N, 15.20.

EXAMPLE 4-35

N-isopropyl-2-isopropyl-3,4-dimethylfuro[2,3-c]pyrazole-5-carboxamide (VIII-35)

The synthesis and purification procedures for preparing compound VIII-1 as described in Example 4-1 were repeated to obtain compound VIII-35 except that isopropylamine (0.60 g, 0.0097 mol) was used instead of ammonia and compound VII-3 (1.0 g, 0.0042 mol) was used instead of compound VII-1. Compound VIII-35 obtained is in light yellow crystal form. Yield, 0.65 g (59%).

mp: 120°-122° C.; IR (KBr) $\nu_{max}$: 3370(NH), 1640(C=O)cm$^{-1}$; UV(CHCl$_3$) $\lambda_{max}$: 286 nm($\epsilon$=1.9×10$^4$); $^1$H-NMR(CDCl$_3$) $\delta$: 1.20-1.33(m,6H,CONHCH(CH$_3$)$_2$), 1.40-1.52(d,6H, —NCH(CH$_3$)$_2$), 2.47(s,3H,C-3—CH$_3$), 2.54(s,3H,C-4—CH$_3$), 3.98-4.67(m,2H,CONHCH(CH$_3$)$_2$, —NCH(CH$_3$)$_2$), 6.00-6.33 (br,1H,—NH); MS, m/z: 263(M+). Anal. Calcd for C$_{14}$H$_{21}$N$_3$O$_2$: C, 63.85; H, 8.04; N, 15.96. Found: C, 63.94; H, 8.15; N, 15.86.

EXAMPLE 4-36

N,N-diethyl-2-isopropyl-3,4-dimethylfuro[2,3-c]pyrazole-5-carboxamide (VIII-36)

The synthesis and purification procedures for preparing compound VIII-1 as described in Example 4-1 were repeated to obtain compound VIII-36 except that diethylamine (0.70 g, 0.0097 mol) was used instead of ammonia and compound VII-3 (1.0 g, 0.0042 mol) was used instead of compound VII-1. Compound VIII-36 obtained is in white crystal form. Yield, 0.65 g (56%).

mp: 80°-82° C.; IR (KBr) $\nu_{max}$: 1620(C=O)cm$^{-1}$; UV(CHCl) $\lambda_{max}$: 293 nm($\epsilon$=3.1×10$^4$); $^1$H-NMR(CDCl$_3$) $\delta$: 1.15-1.45 (t,6H,N(CH$_2$CH$_3$)$_2$), 1.52(d,6H, NCH(CH$_3$)$_2$), 2.47(s,3H, C-3—CH$_3$), 2.54(s,3H,C-4—CH$_3$), 3.33-3.70(q,4H,N(CH$_2$ CH$_3$)$_2$), 4.33-4.67(m,1H,—CH); MS, m/z: 277(M+). Anal. Calcd for C$_{15}$H$_{23}$N$_3$O$_2$: C, 64.96; H, 8.36; N, 15.15. Found: C, 64.87; H, 8.32; N, 15.21.

EXAMPLE 4-37

N-(o-carboxyphenyl)-2-isopropyl-3,4-dimethylfuro[2,3-c]pyrazole-5-carboxamide (VIII-37)

The synthesis and purification procedures for preparing compound VIII-1 as described in Example 4-1 were repeated to obtain compound VIII-37 except that acetonitrile was used as a solvent instead of benzene, 2-aminobenzoicacid (1.40 g, 0.0097 mol) was used instead of ammonia and compound VII-3 (1.0 g, 0.0042 mol) was used instead of compound VII-1. Compound VIII-37 obtained is in light yellow crystal form. Yield, 0.40 g (24%).

mp: 265°-267° C.; IR (KBr) $\nu_{max}$: 3300(NH), 1670(C=O)cm$^{-1}$; UV(C$_2$H$_5$OH) $\lambda_{max}$: 319 nm($\epsilon$=4.1×10$^4$); $^1$H-NMR(DMSO—d$_6$) $\delta$: 1.33-1.50(d,6H,CH(CH$_3$)$_2$), 2.48(m,6H,C-3—CH$_3$,C-4—CH$_3$), 4.33-4.67(m,1H,—CH), 7.00-7.33(m,2H, benzene ring protons), 8.00-8.16(d,1H, benzene ring protons), 8.52-8.70(d,1H, benzene ring protons); MS, m/z: 341(M+). Anal. Calcd for C$_{18}$H$_{19}$N$_3$O$_4$: C, 63.33; H, 5.61; N, 12.31. Found: C, 63.31; H, 5.65, N, 12.39.

EXAMPLE 4-38

N-(o-ethoxycarbonylphenyl)-2-isopropyl-3,4-dimethylfuro[2,3-c]pyrazole-5-carboxamide (VIII-38)

Compound VIII-37 (1.0 g, 0.0033 mol) was dissolved in 100 ml of absolute ethanol, which was then heated under reflux in the presence of concentrated sulfuric acid catalyst. After the reaction was completed, the solvent was evaporated and 10% sodium carbonate solution was added to neutralize the reaction mixture, and the neutralized reaction mixture was subjected to chloroform extraction. The chloroform layer was washed with water for several times, and dried over anhydrous magnesium sulfate, and then the solvent was removed by evaporation. The residue was purified by column chromatography (silica gel-chloroform) to give compound VIII-38 in white crystal form. Yield, 1.0 g (94%).

mp: 155°-158° C.; IR (KBr) $\nu_{max}$: 3250(NH), 1670(C=O)cm$^{-1}$; UV(C$_2$H$_5$OH) $\lambda_{max}$:331 nm($\epsilon$=2.4×10$^4$);H-NMR(DMSO—d$_6$) $\delta$: 1.33-1.54(m,9H,CH(CH$_3$)$_2$,—CH$_2$CH$_3$),2.48(m,6H,C-3—CH$_3$, C-4—CH$_3$), 4.33-4.67(m,3H,—CH(CH$_3$)-$_2$,—CH$_2$CH$_3$), 7.00-7.33(m,2H, benzene ring protons), 8.00-8.16(d,1H, benzene ring protons), 8.72-8.95(d,1H,

EXAMPLE 4-39

2-benzyl-3,4-dimethylfuro[2,3-c]pyrazole-5-carboxylic acid chloride (VII-4)

The synthesis and purification procedures for preparing compound VII-1 as described in Example 4-1 were repeated to obtain compound VII-4 except that compound III-6 (1.0 g, 0.015 mol) was used instead of compound III-1. Compound VII-4 obtained is in yellow brown liquid form.

2-benzyl-3,4-dimethylfuro[2,3-c]pyrazole-5-carboxamide (VIII-39)

Compound VII-4 (1.0 g, 0.0035 mol) was dissolved in benzene (100 ml) and ammonia was bubbled into the solution while heating under reflux. After the reaction was completed, the reaction mixture was filtered, and the solid portion was washed with water and dried. The filtrate portion was washed with water and dried over anhydrous magnesium sulfate and filtered, and then the benzene solvent was evaporated from the filtrate. The residue and the solid portion were combined and purified by column chromatography (silica gel-chloroform) to give compound VIII-1 in white crystal form. Yield, 0.81 g (87%).

mp: 228°-230° C.; IR (KBr) $\nu_{max}$: 3300(NH), 1627(C=O)cm$^{-1}$; UV(CHCl$_3$) $\lambda_{max}$:287 nm($\epsilon$=8.3×10$^4$); $^1$H-NMR(CDCl$_3$) δ: 2.37(s,3H,C-4—CH$_3$), 2.54(s,3H,C-3—CH$_3$), 5.25(s, 2H,—CH$_2$—C$_6$H$_5$), 6.90-7.33(br,2H,—NH$_2$), 7.25(s,5H,—CH$_2$—C$_6$H$_5$); MS, m/z: 269(M+). Anal. Calcd for C$_{15}$H$_{15}$N$_3$O$_2$: C, 66.90; H, 5.61; N, 15.60. Found: C, 66.96; H, 5.67, N, 15.71.

EXAMPLE 4-40

N-methyl-2-benzyl-3,4-dimethylfuro[2,3-c]pyrazole-5-carboxamide (VIII-40)

The synthesis and purification procedures for preparing compound VIII-1 as described in Example 4-1 were repeated to obtain compound VIII-40 except that methylamine was used instead of ammonia and compound VII-4 (1.0 g, 0.0035 mol) was used instead of compound VII-1. Compound VIII-40 obtained is in light yellow crystal form. Yield, 0.75 g (76%).

mp: 142°-144° C.; IR (KBr) $\nu_{max}$: 3450(NH), 1650(C=O)cm$^{-1}$; UV(CHCl$_3$) $\lambda_{max}$: 286 nm ($\epsilon$=1.1×10$^4$); $^1$H-NMR(CDCl$_3$) δ: 2.37(s,3H,C-4—CH$_3$), 2.54(s,3H,C-3—CH$_3$), 2.90-2.98 (d,3H,—NHCH$_3$), 5.25(s,2H,—CH$_2$—C$_6$H$_5$), 6.33-6.55(br,1H,—NH—), 7.25 (s,5H,—CH$_2$—C$_6$H$_5$); MS, m/z: 283(M+). Anal. Calcd for C$_{16}$H$_{17}$N$_3$O$_2$: C, 67.83; H, 6.05; N, 14.83. Found: C, 67.88; H, 6.14; N, 14.93.

EXAMPLE 4-41

N-ethyl-2-benzyl-3,4-dimethylfuro[2,3-c]pyrazole-5-carboxamide (VIII-41)

The synthesis and purification procedures for preparing compound VIII-1 as described in Example 4-1 were repeated to obtain compound VIII-41 except that ethylamine was used instead of ammonia and compound VII-4 (1.0 g, 0.0035 mol) was used instead of compound VII-1. Compound VIII-41 obtained is in light yellow crystal form. Yield, 0.65 g (63%).

mp: 110°-112° C.; IR (KBr) $\nu_{max}$: 3400(NH), 1640(C=O)cm$^{-1}$; UV(CHCl$_3$) $\lambda_{max}$: 286 nm($\epsilon$=6.7×10$^4$); $^1$H-NMR(CDCl$_3$) δ: 1.30-1.58(t,3-H,—NHCH$_2$CH$_3$), 2.37(s,3H,C-4—CH$_3$), 2.54(s,3H,C-3—CH$_3$), 4.34-4.55(q,2H,—NHCH$_2$CH$_3$), 5.25(s,2H,—CH$_2$—C$_6$H$_5$), 6.90-7.33(br,1H,—NH—), 7.25(s,5H,—CH$_2$—C$_6$H$_5$); MS, m/z: 297(M+). Anal. Calcd for C$_{17}$H$_{19}$N$_3$O$_2$: C, 68.67; H, 6.44; N, 14.13. Found: C, 68.74; H, 6.54; N, 14.30.

EXAMPLE 4-42

N-propyl-2-benzyl-3,4-dimethylfuro[2,3-c]pyrazole-5-carboxamide (VIII-42)

The synthesis and purification procedures for preparing compound VIII-1 as described in Example 4-1 were repeated to obtain compound VIII-42 except that propylamine was used instead of ammonia and compound VII-4 (1.0 g, 0.0035 mol) was used instead of compound VII-1. Compound VIII-42 obtained is in light yellow crystal form. Yield, 0.65 g (63%).

mp: 148°-150° C.; IR (KBr) $\nu_{max}$: 3350(NH), 1640(C=O)cm$^{-1}$; UV(CHCl$_3$) $\lambda_{max}$: 285 nm($\epsilon$=2.6×10$^4$); $^1$H-NMR(CDCl$_3$) δ: 0.66-1.25(t,3-H,—NHCH$_2$CH$_2$CH$_3$), 1.33-1.70(m,2-H,—NHCH$_2$CH$_2$CH$_3$), 2.37(s,3H,C-4—CH$_3$), 2.54(s,3H,C-3—CH$_3$), 3.17-3.54(q,2H,—NHCH$_2$-H$_2$—CH$_3$), 5.25(s,2H,—CH2—C$_6$H$_5$), 6.17-6.66(br,1-H,—NH—), 7.25(s,5H,—CH$_2$—C$_6$H$_5$); MS, m/z: 311(M+). Anal. Calcd for C$_{18}$H$_{21}$N$_3$O$_2$: C, 69.43; H, 6.80; N, 13.49. Found: C, 69.40; H, 6.71, N, 13.35.

EXAMPLE 4-43

N-butyl-2-benzyl-3,4-dimethylfuro[2,3-c]pyrazole-5-carboxamide (VIII-43)

The synthesis and purification procedures for preparing compound VIII-1 as described in Example 4-1 were repeated to obtain compound VIII-43 except that butylamine (0.80 g, 0.0097 mol) was used instead of ammonia and compound VII-4 (1.0 g, 0.0035 mol) was used instead of compound VII-1. Compound VIII-43 obtained is in light yellow crystal form. Yield, 0.85 g (74%).

mp: 128°-130° C.; IR (KBr) $\nu_{max}$: 3370(NH), 1640(C=O)cm$^{-1}$; UV(CHCl$_3$) $\lambda_{max}$: 285 nm($\epsilon$=2.0×10$^4$); $^1$H-NMR(CDCl$_3$) δ: 0.95-1.10(t,3-H,—NH(CH$_2$)$_3$CH$_3$), 1.33-1.66(br,4H, —NHCH$_2$(CH$_2$)$_2$CH$_3$), 2.37(s,3H,C-4—CH$_3$), 2.54(s,3H,C-3—CH$_3$), 3.17-3.54(q,2H,—NHC-H$_2$—(CH$_2$)$_2$CH$_3$), 5.25(s,2H,—CH$_2$—C$_6$H$_5$), 6.17-6.66(br,1H,—NH—), 7.25(s,5H,—CH$_2$—C$_6$H$_5$); MS, m/z: 325(M+). Anal. Calcd for C$_{19}$H$_{23}$N$_3$O$_2$: C, 70.13; H, 7.12; N, 12.91. Found: C, 70.30; H, 7.23, N:12.80.

EXAMPLE 4-44

N-isopropyl-2-benzyl-3,4-dimethylfuro[2,3-c]pyrazole-5-carboxamide (VIII-44)

The synthesis and purification procedures for preparing compound VIII-1 as described in Example 4-1 were repeated to obtain compound VIII-44 except that isopropylamine (0.60 g, 0.0097 mol) was used instead of ammonia and compound VII-4 (1.0 g, 0.0035 mol) was used instead of compound VII-1. Compound VIII-44 obtained is in light yellow crystal form. Yield, 0.74 g (69%).

mp: 148°-150° C.; IR (KBr) $\nu_{max}$: 3360(NH), 1640(C=O)cm$^{-1}$; UV(CHCl$_3$) $\lambda_{max}$: 285 nm($\epsilon$=2.0×10$^4$); $^1$H-NMR(CDCl$_3$) δ: 1.10-1.33(d,6-H,—NHCH(CH$_3$)$_2$), 2.37(s,3H,C-4—CH$_3$), 2.54(s,3H,C-3—CH$_3$), 4.00-4.45(m,1H,—NHCH), 5.25(s,2H,—CH$_2$—C$_6$H$_5$), 6.00-6.33(br,1H,—NH—), 7.25(m,5H,—CH$_2$—C$_6$H$_5$); MS, m/z: 311(M+). Anal. Calcd for C$_{18}$H$_{21}$N$_3$O$_2$: C, 69.43; H, 6.80; N, 13.49. Found: C, 69.38; H, 6.62, N, 13.35.

EXAMPLE 4-45

N,N-diethyl-2-benzyl-3,4-dimethylfuro[2,3-c]pyrazole-5-carboxamide (VIII-45)

The synthesis and purification procedures for preparing compound VIII-1 as described in Example 4-1 were repeated to obtain compound VIII-45 except that diethylamine (0.70 g, 0.0097 mol) was used instead of ammonia and compound VII-4 (1.0 g, 0.0035 mol) was used instead of compound VII-1. Compound VIII-45 obtained is in light yellow crystal form. Yield, 0.73 g (65%).

mp: 132°-134° C.; IR (KBr) $\nu_{max}$: 1690(C=O)cm$^{-1}$; UV(CHCl$_3$) $\lambda_{max}$: 299 nm($\epsilon$=9.8×10$^4$); $^1$H-NMR(CDCl$_3$) δ: 1.10-1.38(t,6H,—N(CH$_2$CH$_3$)$_2$), 2.42(s,6H,C-4—CH$_3$,C-3—CH$_3$), 3.33-3.68(q,4-H,—N(CH$_2$CH$_3$)$_2$), 5.25(s,2H,—CH$_2$—C$_6$H$_5$), 7.25(m,5H,—CH$_2$—C$_6$H$_5$); MS, m/z: 325(M+). Anal. Calcd for C$_{19}$H$_{23}$N$_3$O$_2$: C, 70.13; H, 7.12; N, 12.91. Found: C, 70.31; H, 7.22; N, 12.72.

Scheme 6
Part five: preparation of 2,3,4-Trisubstituted-5-hydroxymethylfuro-[2,3-c]pyrazoles (IX)

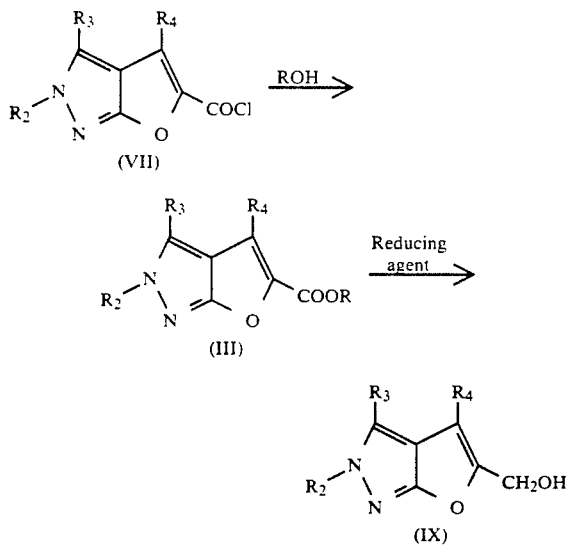

wherein R$_2$, R$_3$ and R$_4$ represent the same meanings as defined above.

Compound VII and an alcohol were heated to undergo esterification reaction to form compound 2,3,4-trisubstituted-5-hydroxymethylfuro[2,3-c]pyrazole-5-carboxylate (III). The resulting ester III was dissolved in a suitable solvent (e.g. THF), and reduced by a suitable reducing agent (e.g. LiAlH$_4$) to give the corresponding 5-hydroxymethyl compound IX which was then purified by column chromatography and recrystalization.

EXAMPLE 5-1 butyl 2-ethyl-3,4-dimethylfuro[2,3-c]pyrazole-5-carboxylate (III-18)

Compound VII-2 (1.0 g, 0.0047 mol) was dissolved in n-butanol (100 ml) and heated under reflux for four hours. The solvent was evaporated from the reaction solution, and the residue thereof was purified by column chromatography (silica gel-chloroform) to give compound III-18 in light yellow liquid. Yield, 1.0 g (79%).

IR (KBr) $\nu_{max}$: 1700(C=O)cm$^{-1}$; UV (CHCl) $\lambda_{max}$: 276 nm; $^1$H-NMR(CDCl$_3$) δ: 0.93(t,3H,—(CH$_2$)$_3$CH$_3$), 1.27-1.80(m,7H,—OCH$_2$CH$_2$CH$_2$CH$_3$,N—CH$_2$CH$_3$), 2.47(s,3H,C-4—CH$_3$), 2.50(s,3H,C-3—CH$_3$), 3.87-4.43(m,4H,—OCH$_2$CH$_2$CH$_2$CH$_3$,N—CH$_2$CH$_3$); MS, m/z: 264(M+). Anal. Calcd for: C$_{14}$H$_{20}$N$_2$O$_3$: C, 63.62; H, 7.63; N, 10.60. Found: C, 62.55, H, 7.70; N, 10.72.

5-hydroxymethyl-2-ethyl-3,4-dimethylfuro[2,3-c]pyrazole (IX)

Lithium aluminum hydride (0.5 g, 0.013 mol) was added to 30 ml of anhydrous ethyl ether, and then an ethyl ether solution containing 0.5 g (0.0019 mol) of compound III-18 was added dropwise and slowly. The resulting mixture was stirred at room temperature. After the reaction was completed, 1 ml of water was added to the reaction mixture while stirring, which was then filtered and the filtrate was dried over anhydrous magnesium sulfate, and finally the solvent was removed by evaporation. The residue was purified by column chromatography (silica gel-chloroform) to give compound IX in white crystal form. Yield, 0.3 g (81%).

mp: 124°-126° C.; IR (KBr) $\nu_{max}$: 3250(OH)cm$^{-1}$; UV(CHCl$_3$) $\lambda_{max}$: 252 nm; $^1$H-NMR(CDCl$_3$) δ: 1.38(t,3H,N—CH$_2$CH$_3$), 2.15(s,3H,C-4—CH$_3$), 2.38(s,3H,C-3—CH$_3$), 4.07(q,2H,N—CH$_2$CH$_3$), 4.57(s,2H,—CH$_2$OH); MS, m/z: 194(M+). Anal. Calcd for C$_{10}$H$_{14}$N$_2$O$_2$: C, 61.84; H, 7.26; N, 14.42. Found: C, 61.95; H, 7.32; N, 14.50.

Scheme 7
Part six: preparation of 2,3,4-Trisubstituted-5-(2,3-dihydro-2-oxo-1,3,4-oxadiazol-5-yl)furo[2,3-c]pyrazoles (XI)

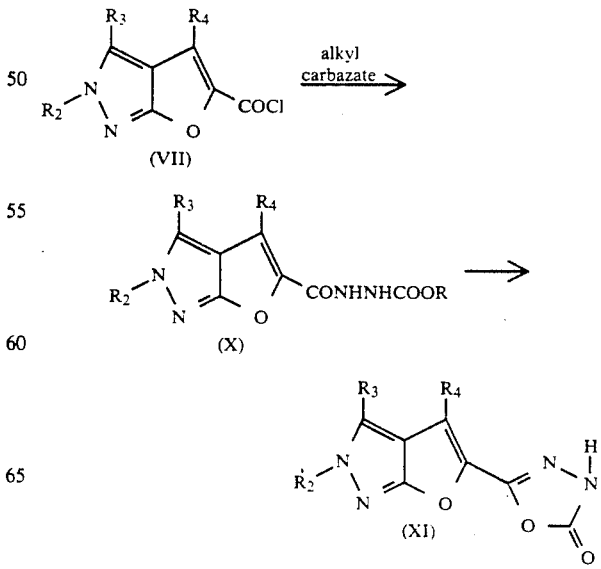

-continued
Scheme 7 wherein $R_2$, $R_3$ and $R_4$ represent the same meanings as defined above.

Compound VII was dissolved in a suitable solvent (e.g. acetonitrile) and reacted with alkyl carbazate to obtain N-alkoxycarbonylamino-2,3,4-trisubstituted furo-[2,3-c]pyrazole-6-carboxamides (X). The intermediate X was dissolved in a suitable solvent (e.g. diphenylether) and heated to undergo cyclization reaction to form the desired compound 5-(2,3-dihydro-2-oxo-1,3,4-oxadiazol-5-yl)-2,3,4-trisubstituted furo-[2,3-c]pyrazoles (XI).

EXAMPLE 6-1

N-(ethoxycarbonylamino)-2,3,4-trimethylfuro[2,3-c]pyrazole-5-carboxamide (X-1)

The synthesis and purification procedures for preparing compound VIII-1 as described in Example 4-1 were repeated to obtain compound X-1 except that ethyl carbazate (0.70 g, 0.0097 mol) was used instead of ammonia and acetonitrile was used instead of benzene as a solvent. Compound X-1 obtained is in yellow crystal form. Yield, 0.75 g (55%).

mp: 218°–219° C.; IR (KBr) $\nu_{max}$: 3360 (NH), 1730(COOC$_2$H$_5$), 1660 (CONHNH)cm$^{-1}$; UV(CHCl$_3$) $\lambda_{max}$: 287 nm ($\epsilon$=2.2×10$^4$); $^1$H-NMR (CDCl$_3$) $\delta$: 1.05–1.33(t,3H,—CH$_2$CH$_3$), 2.47(s,6H,C-4—CH$_3$,C-3—CH$_3$), 3.83(s,3H,—NCH$_3$), 3.90–4.25(q,2-H,—CH$_2$CH$_3$), 8.85–9.00(br,1H,—NHNH), 9.90–10.0(br,1H,—NHNH); MS, m/z: 280(M+). Anal. Calcd for C$_{12}$H$_{16}$N$_4$O$_4$: C, 51.42; H, 5.75; N, 19.99. Found: C,51.49, H:5.68; N, 19.85.

5-(2,3-dihydro-2-oxo-1,3,4-oxadiazol-5-yl)-2,3,4-trimethylfuro[2,3-c]pyrazoles (XI-1)

To diphenylether solvent (100 ml) which was heated to a temperature of 240° C., compound X-1 (1.0 g, 0.0036 mol) was added and the solution was heated under reflux. After the reaction was completed, the reaction mixture was cooled and filtered. The precipitate was washed with n-hexane and dried, and then was recrystallized from ethanol to give compound XI-1 in light yellow crystal form. Yield, 0.85 g (98%).

mp: 236°–239° C.; IR (KBr) $\nu_{max}$: 3050(NH), 1780(C=O)cm$^{-1}$; UV (C$_2$H$_5$OH) $\lambda_{max}$: 287 nm($\epsilon$=3.0×10$^4$); $^1$H-NMR(DMSO—d$_6$) $\delta$: 2.45(s,6H,C-4—CH$_3$,C-3—CH$_3$), 3.83(s,3H,—NCH$_3$); MS, m/z: 234(M+). Anal. Calcd for C$_{10}$H$_{10}$N$_4$O$_3$: C, 51.28; H, 4.30; N, 23.92. Found: C, 51.34; H, 4.39; N, 23.90.

EXAMPLE 6-2

N-(ethoxycarbonylamino)-2-ethyl-3,4-dimethyl-furo[2,3-c]pyrazole-5-carboxamide (X-2)

The synthesis and purification procedures for preparing compound X-1 as described in Example 6-1 were repeated to obtain compound X-2 except that N-ethyl carbazate (0.70 g, 0.0097 mol) was used instead of ammonia and compound VII-2 (1.0 g, 0.0044 mol) was used instead of compound VII-1. Compound X-2 obtained is in light yellow crystal form. Yield, 0.65 g (50%).

mp: 225°–226° C.; IR (KBr) $\nu_{max}$: 3290–3230(NH), 1740(COOC$_2$H$_5$), 1660(CONHNH)cm$^{-1}$; UV(CHCl$_3$) $\lambda_{max}$: 280 nm($\epsilon$=1.4×10$^4$); $^1$H-NMR(CDCl$_3$) $\delta$: 1.36(t,3H,N—CH$_2$CH$_3$), 1.52(t,3H,COOCH$_2$CH$_3$), 2.46(s,3H,C-4—CH$_3$), 2.55(s,3H,C-3—CH$_3$), 4.19(q,2H,N—CH$_2$CH$_3$), 4.23(q,2H,COOCH$_2$CH$_3$); MS, m/z: 294(M+). Anal. Calcd for C$_{13}$H$_{18}$N$_4$O$_4$: C, 53.05; H, 6.16; N, 19.04. Found: C, 53.16; H, 6.20; N, 19.24.

5-(2,3-dihydro-2-oxo-1,3,4-oxadiazol-5-yl)-2-ethyl-3,4-dimethylfuro[2,3-c]pyrazoles (XI-2)

To diphenylether solvent (100 ml) which was heated to a temperature of 240° C., compound X-2 (1.0 g, 0.0034 mol) was added and the solution was heated under reflux. After the reaction was completed, the reaction mixture was cooled and filtered. The precipitate was washed with n-hexane and dried, and then was purified by column chromatography (silica gel-ethyl acetate) to compound XI-2 in light yellow crystal form. Yield, 0.80 g (95%).

mp: 243°–245° C. (dec.); IR (KBr) $\nu_{max}$: 3100(NH), 1760(C=O)cm$^{-1}$; UV(C$_2$H$_5$OH) $\lambda_{max}$: 296 nm($\epsilon$=5.2×10$^4$); $^1$H-NMR(DMSO—d$_6$) $\delta$:1.33(t,3H,N—CH$_2$CH$_3$), 2.46(s,6H,C-4—CH$_3$, C-3—CH$_3$), 4.17(q,2H,N—CH$_2$CH$_3$); MS, m/z: 248(M+). Anal. Calcd for C$_{11}$H$_{12}$N$_4$O$_3$: C, 53.22; H, 4.87; N, 22.57. Found: C, 53.41; H, 4.90; N, 22.60.

EXAMPLE 6-3

N-(ethoxycarbonylamino)-2-isopropyl-3,4-dimethyl-furo[2,3-c]pyrazole-5-carboxamide (X-3)

The synthesis and purification procedures for preparing compound X-1 as described in Example 6-1 were repeated to obtain compound X-3 except that N-ethyl carbazate (0.70 g, 0.0097 mol) was used instead of ammonia and compound VII-3 (1.0 g, 0.0042 mol) was used instead of compound VII-1. Compound X-3 obtained is in light yellow crystal form. Yield, 0.65 g (50%).

mp: 160°–163° C.; IR (KBr) $\nu_{max}$: 3320–3200(NH), 1730(COOC$_2$H$_5$), 1640(CONHNH)cm$^{-1}$; UV(CHCl$_3$) $\lambda_{max}$:287nm($\epsilon$=4.5×10$^3$); $^1$H-NMR(CDCl$_3$) $\delta$:1.17–1.42(t,3H,COOCH$_2$CH$_3$), 1.47–1.54 (d,6H,—CH(CH$_3$)$_2$), 2.46(s,3H,C-4—CH$_3$), 2.55(s,3H,C-3—CH$_3$), 4.00–4.67(m,3H,N—CH(CH$_3$)$_2$,COOCH$_2$CH$_3$); MS, m/z: 308(M+). Anal. Calcd for C$_{14}$H$_{20}$N$_4$O$_4$: C, 54.54; H, 6.54; N, 18.17. Found: C, 54.60; H, 6.60; N, 18.23.

5-(2,3-dihydro-2-oxo-1,3,4-oxadiazol-5-yl)-2-isopropyl-3,4-dimethylfuro[2,3-c]pyrazoles (XI-3)

The synthesis and purification procedures for preparing compound XI-1 as described in Example 6-1 were repeated to obtain compound XI-3 except that compound X-3 (1.0 g, 0.0032 mol) was used instead of compound X-1. Compound XI-3 obtained is in light yellow crystal form. Yield, 0.77 g (93%).

mp: 195°–198° C.; IR (KBr) $\nu_{max}$: 3100(NH), 1780(C=O)cm$^{-1}$; UV(CHCl$_3$) $\lambda_{max}$: 300 nm($\epsilon$=9.2×10$^3$); $^1$H-NMR(DMSO—d$_6$) $\delta$:1.33–1.50(d,6H,CH(CH$_3$)$_2$), 2.43(s,3H,C-4—CH$_3$), 2.33(s,3H,C-3—CH$_3$), 4.52(m,1H,—CH—); MS, m/z: 262(M+). Anal. Calcd for C$_{12}$H$_{14}$N$_4$O$_3$: C, 54.96; H, 6.38; N, 21.36. Found: C, 54.99; H, 6.30; N, 21.47.

EXAMPLE 6-4

N-(ethoxycarbonylamino)-2-benzyl-3,4-dimethyl-furo[2,3-c]pyrazole-5-carboxamide (X-4)

The synthesis and purification procedures for preparing compound X-1 as described in Example 6-1 were repeated to obtain compound X-4 except that N-ethyl carbazate (0.70 g, 0.0097 mol) was used instead of ammonia and compound VII-4 (1.0 g, 0.0038 mol) was used instead of compound VII-1. Compound X-4 obtained is in light yellow crystal form. Yield, 0.90 g (67%).

mp: 220°-222° C.; IR (KBr) $\nu_{max}$: 3200(NH), 1740(COOC$_2$H$_5$), 1640(CONHNH)cm$^{-1}$; UV(CHCl$_3$) $\lambda_{max}$: 288 nm($\epsilon$=4.2×10$^4$); $^1$H-NMR(CDCl$_3$) $\delta$:0.95-1.25(t,3H,COOCH$_2$CH$_3$), 2.46 (s,6H,C-4—CH$_3$,C-3—CH$_3$), 3.90-4.33(q,2H,—COOCH$_2$—CH$_3$), 5.25(s,2H,—CH$_2$—C$_6$H$_5$), 7.25(m,5H,—CH$_2$—C$_6$H$_5$); MS, m/z: 356(M+). Anal. Calcd for C$_{18}$H$_{20}$N$_4$O$_4$: C, 60.66; H, 5.66; N, 15.72. Found: :C, 60.71; H, 5.62; N, 15.73.

5-(2,3-dihydro-2-oxo-1,3,4-oxadiazol-5-yl)-2-benzyl-3,4-dimethylfuro[2,3-c]pyrazoles (XI-4)

The synthesis and purification procedures for preparing compound XI-1 as described in Example 6-1 were repeated to obtain compound XI-4 except that compound X-4 (1.0 g, 0.0028 mol) was used instead of compound X-1. Compound XI-4 obtained is in light yellow crystal form. Yield, 0.80 g (92%).

mp: 240°-243° C.; IR (KBr) $\nu_{max}$: 3000(NH), 1710(C=O)cm$^{-1}$; UV (C$_2$H$_5$OH) $\lambda_{max}$: 302 nm($\epsilon$=1.2×10$^4$); $^1$H-NMR(DMSO-d$_6$) $\delta$:2.47(s,6H,C-4—CH$_3$, C-3—CH$_3$), 5.37(s, 2H,—CH$_2$—C$_6$H$_5$), 7.25(m,5H,—CH$_2$—C$_6$H$_5$); MS, m/z: 310(M+). Anal. Calcd for C$_{16}$H$_{14}$N$_4$O$_3$: C, 61.93; H, 4.55; N, 18.06. Found: C, 61.96; H, 4.62; N, 18.17.

Scheme 8
Part seven: preparation of 2-(2,3-Dihydro-2-oxo-3-acyl)-1,3,4-oxadiazol-5-yl)-2,3,4-trisubstituted-furo[2,3-c]pyrazoles (XII)

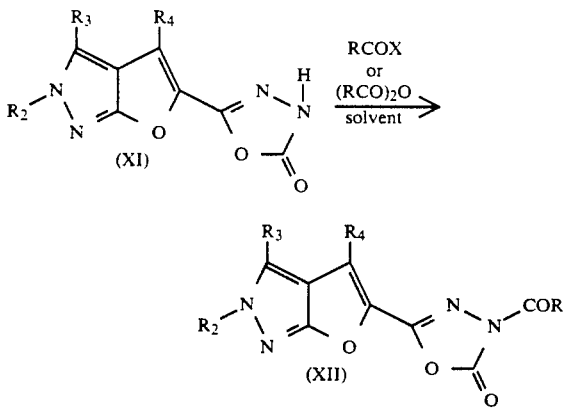

wherein R$_2$, R$_3$ and R$_4$ represent the same meanings as defined above.

Compound XI was dissolved in a suitable solvent (e.g. acetic acid) and reacted with a suitable acylation agent (e.g. acetic anhydride) to obtain the acylated compound XII.

EXAMPLE 7-1

5-(2,3-dihydro-2-oxo-3-acetyl-1,3,4-oxadiazol-5-yl)-2-methyl-3,4-dimethylfuro[2,3-c]pyrazoles (XII-1)

Compound XI-1 (1.0 g, 0.0043 mol) was dissolved in 10 ml of acetic acid and 1 ml of acetic anhydride, and the resulting solution was heated to 100° C. and react for one hour. The reaction mixture was then poured to cool water, followed by filtration. The precipitate collected was washed with water and dried to give compound XII-1 in yellow crystal form. Yield, 1.0 g (85%).

mp: 236°-239° C.; IR (KBr) $\nu_{max}$: 3050(NH), 1720(C=O)cm$^{-1}$; UV(C$_2$H$_5$OH) $\lambda_{max}$: 314 nm($\epsilon$=3.5×10$^3$); $^1$H-NMR(DMSO-d$_6$) $\delta$:2.45(m,9H,C-4—CH$_3$,C-3—CH$_3$,—COCH$_3$), 3.83(s,3H,N—CH$_3$); MS, m/z:276(M+). Anal. Calcd for C$_{12}$H$_{12}$N$_4$O$_4$: C, 52.17; H, 4.38; N, 20.28. Found: :C, 52.20; H, 4.43, N:20.32.

EXAMPLE 7-2

5-(2,3-dihydro-2-oxo-3-acetyl-1,3,4-oxadiazol-5-yl)-2-ethyl-3,4-dimethylfuro[2,3-c]pyrazoles (XII-2)

The synthesis and purification procedures for preparing compound XII-1 as described in Example 7-1 were repeated to obtain compound XII-2 except that compound XI-2 (1.0 g, 0.0040 mol) was used instead of compound XI-1. Compound XII-2 obtained is in light yellow crystal form. Yield, 1.0 g (81%).

mp: 208°-210° C.; IR (KBr) $\nu_{max}$: 3300(NH), 1740(C=O), 1640(C=O)cm$^{-1}$; UV(C$_2$H$_5$OH) $\lambda_{max}$: 311nm($\epsilon$=5.5×10$^3$); $^1$H-NMR(DMSO-d$_6$) $\delta$:1.33(t,3H,N—CH$_2$CH$_3$), 2.46(m,9H,C-4—CH$_3$,C-3—CH$_3$,—COCH$_3$), 4.17(q,2H,N—CH$_2$CH$_3$); MS, m/z: 290(M+). Anal. Calcd for C$_{13}$H$_{14}$N$_4$O$_4$: C, 53.79, H, 4.86; N, 19.30. Found: C, 53.82; H, 4.74; N, 19.26.

EXAMPLE 7-3

5-(2,3-dihydro-2-oxo-3-acetyl-1,3,4-oxadiazol-5-yl)-2-isopropyl-3,4-dimethylfuro[2,3-c]pyrazoles (XII-3)

The synthesis and purification procedures for preparing compound XII-1 as described in Example 7-1 were repeated to obtain compound XII-3 except that compound XI-3 (1.0 g, 0.0038 mol) was used instead of compound XI-1. Compound XII-3 obtained is in yellow crystal form. Yield, 0.90 g (77%).

mp: 208°-210° C.; IR (KBr) $\nu_{max}$: 3000(NH), 1730(C=O), 1640(C=O)cm$^{-1}$; UV(CHCl$_3$) $\lambda_{max}$: 314 nm($\epsilon$=3.5×10$^4$); $^1$H-NMR(DMSO—d$_6$) $\delta$:1.33-1.50(d,6H(t,3H,CH(CH$_3$)$_2$), 2.48(m,9H,C-4—CH$_3$,C-3—CH$_3$, —COCH$_3$), 4.33-4.67(m,1-H,—CH); MS, m/z: 304(M+). Anal. Calcd for C$_{14}$H$_{16}$N$_4$O$_4$: C, 55.26; H, 5.30; N, 18.41. Found: C, 55.40; H, 5.51; N, 18.46.

EXAMPLE 7-4

5-(2,3-dihydro-2-oxo-3-acetyl-1,3,4-oxadiazol-5-yl)-2-benzyl-3,4-dimethylfuro[2,3-c]pyrazoles (XII-4)

The synthesis and purification procedures for preparing compound XII-1 as described in Example 7-1 were repeated to obtain compound XII-4 except that compound XI-4 (1.0 g, 0.0032 mol) was used instead of compound XI-1. Compound XII-4 obtained is in light yellow crystal form. Yield, 1.0 g (88%).

mp: 168°-170° C.; IR (KBr) $\nu_{max}$: 3200(NH), 1740(C=O), 1640(C=O)cm$^{-1}$; UV(C$_2$H$_5$OH) $\lambda_{max}$: 297 nm($\epsilon$=2.0×10$^4$); $^1$H-NMR(DMSO—d$_6$)

δ:2.47(m,9H,C-4—CH$_3$, C-3—CH$_3$,—COCH$_3$), 5.37(s,2H,—CH$_2$—C$_6$H$_5$), 7.25(m,5H,—CH$_2$—C$_6$H$_5$); MS, m/z: 352(M$^+$). Anal. Calcd for C$_{18}$H$_{16}$N$_4$O$_4$: C, 61.36, H:4.58; N, 15.90. Found: :C, 61.40; H, 4.63; N, 15.96.

ence of a base (e.g. piperidine) under heating. The condensation reaction product was acidified and purified by column chromatography and recrystalization to give compound XIII.

Scheme 9
Part eight: preparation of 2,3,4-Trisubtituted furo[2,3-c]pyrazole-5-acrylic acid (XIII) and its esters (XVII)

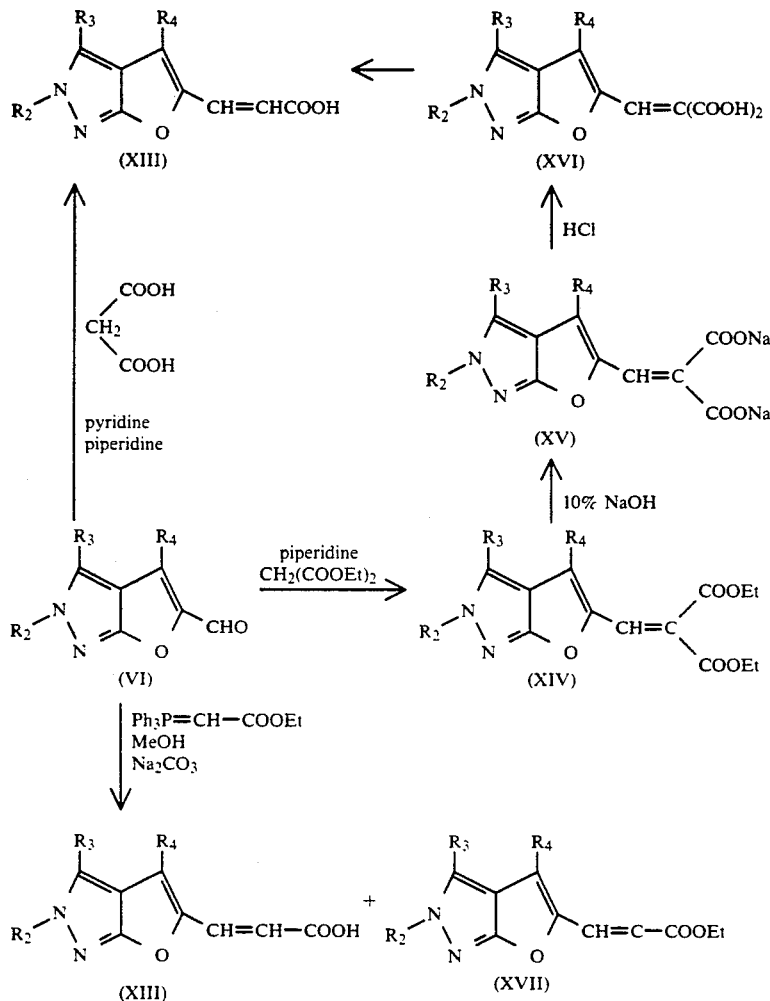

wherein R$_2$, R$_3$ and R$_4$ represent the same meanings as defined above.

As illustrated in scheme 9, there are three methods to synthesize compound XIV.

Method I

An aldehyde V was dissolved in a suitable solvent (e.g. benzene) and a condensation reaction was carried out in the presence of a base (e.g. piperidine) by heating the solution to form 2,3,4-trisubstituted furo[2,3-c]pyrazol-5-ylmethylidene malonate (XIV) which was purified by column chromatography and recrystalization. The compound XIV was hydrolized with a strong alkali (e.g. NaOH) and then acidified with a mineral acid (e.g. HCl), and finally was recrystallized from a suitable solvent to give the corresponding acrylic acid XIII.

Method II

Malonic acid was dissolved in a suitable solvent (e.g. pyridine), and condensed with compound V in the pres-

Method III

A Wittig reagent (Ph$_3$P=CHCOOR) was dissolved in a suitable solvent (e.g. methanol) and a Whitting reaction with compound V was carried out under a weak base condition to form 2,3,4-trisubstituted furo[2,3-c]pyrazol-5-acrylate (XVII) and a portion of hydrolized acrylic acid XIII.

EXAMPLE 8-1

2,3,4-trimethylfuro[2,3-c]pyrazole-5-acrylic acid (XIII-1)

Method II

To the solution of dry malonic acid (1.0 g, 0.0097 mol) in pyridine (20 ml, 0.25 mol), compound V-1 (0.623 g, 0.0035 mol) and piperidine (1.0 ml, 0.011 mol) were added in sequence, and the resulting mixture was heated to 110°-115° C. under reflux for two hours, and then benzene was added to remove the organic solvents thereform by evaporation, and finally ice water was added to form crystal. The precipitate was collected by filtration and washed with water, and then was dissolved in 10% sodium hydrogen carbonate solution, and washed with chloroform. The aqueous layer was acidified with 10% HCl solution while stirring and cooling, which was then put into an ice bath for one hour to precipitate. The precipitate was collected by filtration, washed with water and dried. The residue was purified by column chromatography (silica gel-chloroform & ethanol) to give compound XIII-1 in yellow crystal form. Yield, 0.60 g (78%).

mp: 254°-256° C.; IR(KBr) $\nu_{max}$:2700-3000(COOH), 1685(CH=CH—COOH)cm$^{-1}$; UV(CHCl$_3$) $\lambda_{max}$: 350 nm; $^1$H-NMR(DMSO—d$_6$) $\delta$: 2.28(s,3H,C-4—CH$_3$), 2.43(s,3H,C-3—CH$_3$), 3.70(s,3H,N—CH$_3$), 5.97(d,1H,J=16 Hz, —CH=CHCOOH), 7.37(d,1H,J=16 Hz,—CH=CH—COOH); MS, m/z: 220(M$^+$). Anal. Calcd for C$_{11}$H$_{12}$N$_2$O$_3$: C, 59.99; H, 5.49; N, 12.72. Found: C, 60.08; H, 5.54; N, 12.62.

Method I 2,3,4-trimethylfuro[2,3-c]pyrazol-5-yl-methylidene malonate (XIV-1)

To the solution of compound V-1 (0.623 g, 0.0035 mol) in 80 ml benzene, diethyl malonate (1.5 g, 0.0090 mol) and piperidine (1 ml, 0.011 mol) were added, and the mixture was heated under reflux for two hours while removing the water formed by the reaction. After the reaction was completed, the reaction mixture was washed with water and dried over anhydrous magnesium sulfate, and the solvent was removed therefrom by evaporation. The residue was purified by column chromatography (silica gel-chloroform) to give compound XIV-1 in yellow crystal form. Yield, 1.10 g (61%).

mp: 76°-78° C.; IR (KBr) $\nu_{max}$: 1730(C=O), 1700(C=O)cm$^{-1}$; $^1$H-NMR(CDCl$_3$) $\delta$: 1.07-1.73(m,6H,C(COOCH$_2$CH$_3$)$_2$), 2.30(s,3H,C-4—CH$_3$), 2.40(s,3H,C-3—CH$_3$), 3.77(s,3H,N—CH$_3$), 3.90-4.60(m,4H,C(COOCH$_2$CH$_3$)$_2$), 7.37(s,1H,—CH=C<); MS, m/z: 320(M$^+$).

2,3,4-trimethylfuro[2,3-c]pyrazole-5-acrylic acid (XIII-1)

The compound XIV-1 was suspended in 10% NaOH solution, and stirred at 70° C. for eight hours, which was then filtered. The filtrate was washed with ethyl ether, and acidified with 10% HCl solution while stirring and cooling, which was then put into an ice bath for one hour to precipitate. The precipitate was collected by filtration, washed with water and dried. The residue was recrystallized from ethanol to give compound XIII-1 in yellow crystal form. Yield, 0.42 g (63%). mp: 254°-256° C. IR and TLC of this product were compared with those of compound XIII-1 obtained by method II, and a mixed melting point test was conducted, and the results show the compounds prepared by method II and I are the same compound.

Method III methyl-2,3,4-trimethyluro[2,3-c]pyrazole-5-acrylate (XVII-1)

To a solution of ethyl chloroacetate (0.4 g, 0.0028 mol) in 15 ml benzene, triphenylphosphine (0.75 g, 0.0028 mol) was added, which was then heated under reflux for two hours to form precipitate yield, Ph$_3$P=CH—COOEt. A Whitting agent was prepared. The precipitate was dissolved in 20 ml methanol, and compound V-1 (0.50 g, 0.0028 mol) was added followed by adding 10% sodium carbonate solution at room temperature. After the reaction was completed, methanol was removed from the reaction mixture by evaporation, which was then extracted with chloroform. The extract was dried over anhydrous magnesium sulfate, filtered and the solvent was removed from the filtrate by evaporation. The residue was purified by column chromatography (silica gel-chloroform) and recrystallized from ethanol to give compound XVII-1 in yellow needle crystal form. Yield, 0.29 g (45%).

mp: 146°-148° C.; IR (KBr) $\nu_{max}$: 1710(—CH=CH—CO)cm$^{-1}$; UV(CHCl$_3$) $\lambda_{max}$: 344 nm; $^1$H-NMR(CDCl$_3$) $\delta$: 2.13(s,3H,C-4—CH$_3$), 2.30(s,3H,C-3—CH$_3$), 3.70(s,6H,N—CH$_3$ and O—CH$_3$), 6.10(d,1H,J=16 Hz,—CH=CH—CO), 7.33(d,1H,J=16 Hz,—CH=CH—COOCH$_3$); MS, m/z: 234(M$^+$), 203(M$^+$-31).

2,3,4-trimethylfuro[2,3-c]pyrazole-5-acrylic acid (XIII-1)

The aqueous layer obtained from the extraction was acidified with 10% HCl solution, and yellow precipitate was formed. The precipitate was collected by filtration and washed with water, and then was dissolved in 10% sodium hydrogen carbonate solution, and washed with chloroform. The aqueous layer was acidified with 10% HCl solution while stirring and cooling, which was then put into an ice bath for one hour to precipitate. The precipitate was collected by filtration, washed with water and dried. The residue was purified by column chromatography (silica gel-chloroform & ethanol) to give compound XIII-1 in yellow crystal form. Yield, 0.31 g (39%). mp: 254°-256° C. IR and TLC of this product were compared with those of compounds XIII-1 obtained by method I and II, and a mixed melting point test was conducted, and the results show the compounds prepared by method I, II and III are the same compound.

EXAMPLE 8-2

2-ethyl-3,4-dimethylfuro[2,3-c]pyrazole-5-acrylic acid (XIII-2)

To the solution of dry malonic acid (1.0 g, 0.0097 mol) in pyridine (20 ml, 0.25 mol), compound V-2 (0.67 g, 0.0035 mol) and piperidine (1.0 ml, 0.011 mol) were added in sequence, and the resulting mixture was heated to 110°-115° C. under reflux for two hours, and then benzene was added to remove the organic solvents thereform by evaporation, and finally ice water was added to form crystal. The precipitate was collected by filtration and washed with water, and then was dissolved in 10% sodium hydrogen carbonate solution, and washed with chloroform several times in separatory funnel. The aqueous layer was acidified with 10% HCl solution while stirring and cooling, which was then put into an ice bath for one hour to precipitate. The precipitate was collected by filtration, washed with water and dried. The residue was purified by column chromatography (silica gel-chloroform & ethanol) to give compound XIII-2 in yellow crystal form. Yield, 0.67 g (82%).

mp: 215°-217° C.; IR (KBr) $\nu_{max}$: 3100-2500(OH), 1690(C=O), 1600 (—CH=CH—COOH)cm$^{-1}$; UV ($C_2H_5OH$) $\lambda_{max}$: 355 nm; $^1$H-NMR(DMSO—d$_6$) δ: 1.30(t,3H,N—CH$_2$CH$_3$), 2.25(s,3H,C-4—CH$_3$), 2.42(s,3H,C-3—CH$_3$), 4.06(q,2H,N—CH$_2$CH$_3$), 5.97(d,1H,J=16 Hz,—CH=CH—COOH), 7.37(d,1H,J=16 Hz,—CH=CH—COOH); MS, m/z: 234(M$^+$). Anal. Calcd for $C_{12}H_{14}N_2O_3$: C, 61.53; H, 6.02; N, 11.96. Found: C, 61.60; H, 6.15; N, 11.99.

ethyl 2-ethyl-3,4-dimethylfuro[2,3-c]pyrazole-5-acrylate (XVII-2)

Compound XIII-2 (1.0 g, 0.0043 mol) was dissolved in 100 ml absolute ethanol. After adding conc. sulfuric acid as a catalyst, the solution was heated under reflux until the reaction was completed. The solvent was then removed from the reaction mixture by evaporation, and 10% sodium carbonate solution was added to neutralize the remaining reaction mixture, followed by extracting with ethyl ether. The extract was washed with water for several times, dried over anhydrous magnesium sulfate, filtered and the solvent was removed from the filtrate by evaporation. The residue was purified by column chromatography (silica gel-chloroform) to give compound XVII-2 in light yellow crystal form. Yield, 0.76 g (68%).

mp: 109°-112° C.; IR (KBr) $v_{max}$: 1700(C=O), 1600(C=C)cm$^{-1}$; UV(CHCl$_3$) $\lambda_{max}$: 348 nm; $^1$H-NMR(CDCl$_3$) δ: 1.32(t,3H,N—CH$_2$CH$_3$), 1.42(t,3H,—COOCH$_2$CH$_3$), 2.27(s,3H,C-4—CH$_3$), 2.43(s,3H,C-3—CH$_3$), 4.10(q,2H,N—CH$_2$CH$_3$), 4.79(q,2H,—COOCH$_2$CH$_3$), 6.28(d,1H,J=16 Hz, —CH=CH—COOH), 7.48(d,1H,J=16 Hz,—CH=CH—COOH); MS, m/z: 262(M$^+$). Anal. Calcd for $C_{14}H_{18}N_2O_3$: C, 64.11; H, 6.92; N, 10.68. Found: C, 64.11; H, 6.98; N, 10.75.

Scheme 10
Part nine: preparation of 2,3,4-Trisubstituted furo[2,3-c]pyrazole-5-acrylamides (XIX)

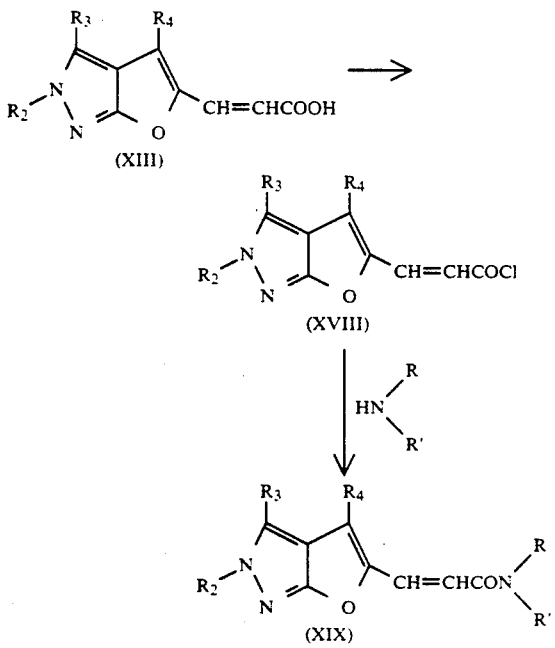

wherein R$_2$, R$_3$ and R$_4$ represent the same meanings as defined above.

Compound XIII was dissolved in a suitable solvent (e.g. benzene) and treated with SOCl$_2$ to undergo chlorination reaction. The chlorination reaction product, i.e. acid chloride intermediate XVIII, was purified by recrystalization from a suitable solvent (e.g. petroleum ether+ethyl ether). The intermediate XVIII was dissolved in a suitable solvent (e.g. benzene) and reacted with an amine to form the desired compound XIX.

EXAMPLE 9-1

2-ethyl-3,4-dimethylfuro[2,3-c]pyrazole-5-acrylic acid chloride (XVIII-2)

To a solution of compound XIII-2 (1.0 g, 0.0043 mol) in anhydrous benzene (100 ml), thionyl chloride (4.1 g, 0.035 mol) was added. The mixture was heated while stirring until the reaction was completed. The solvent was removed from the reaction mixture by evaporation, and the residue was washed with petroleum ether and dried to give compound XVIII-2. Yellow brown raw product. Yield, 1.1 g (92%).

2-ethyl-3,4-dimethylfuro[2,3-c]pyrazole-5acrylamide (XIX-2)

Compound XVIII-2 (1.0 g, 0.0040 mol) was dissolved in 100 ml anhydrous benzene, and ammonia was bubbled into the solution while stirring. After the reaction was completed, the reaction mixture was filtered and the solid portion collected was washed with water and dried. The filtrate was washed with water for several times, dried over anhydrous magnesium sulfate and filtered, and finally the benzene solvent was evaporated from the filtrate. The residue and the solid portion were combined and recrystallized from ethanol-chloroform mixed solvent to give compound XIX-2 in yellow crystal form. Yield, 0.54 g (58%).

mp: 258°-260° C.; IR (KBr) $v_{max}$: 3190, 3380(NH), 1660(C=O), 1600(C=C)cm$^{-1}$; UV ($C_2H_5OH$) $\lambda_{max}$: 333 nm; $^1$H-NMR(DMSO—d$_6$) δ: 1.30(t,3H,N—CH$_2$CH$_3$), 2.27(s,3H,C-4—CH$_3$), 2.43(s,3H,C-3—CH$_3$), 4.07(q,2H,N—CH$_2$CH$_3$), 6.27(d,1H,J=16 Hz,—CH=CH—CONH$_2$), 7.23(d,1H,J=16 Hz,—CH=CH—CONH$_2$); MS, m/z: 233(M$^+$). Anal. Calcd for $C_{12}H_{15}N_3O_2$: C, 61.79; H, 6.48; N, 18.01. Found: C, 61.82; H, 6.53; N, 18.17.

Pharmacological Experiment

I. Rat PCA Test

Wistar male rats (150–220 g) were used as the experiment animal. 0.1 ml of diluted anti-Serum to ovalbumin were injected (s. c) in 2 sites of the abdomene of the rats. After 48 hours from the injections, 2 mg of eggalbumin antigen in 0.5% Evans blue solutions 1 ml were injected through the caudal veins. About 30 minutes later, the rats were killed and the skin of the abdomen were stripped. The size and depth of the blue area were measured, and the mean of the measured data were taken as a response value. Test compounds were dissolved or suspended in the physiological saline or 0.5% aqueous gum tragacanth, and administrated 5 minutes before (s. c) or one hour before (oral) the Evans blue solution injections.

II. Antithrombocyte aggregation test (A). Preparation of thrombocyte inducing agent 1. Collagen (bovin tendon) in 15 mM aqueous acetic acid was grounded at 4° C. to form a well dispersed suspension, and dispensed in 1 mg/ml and stocked at −70° C. Before using, it was thawed and well grounded.

2. PAF was dissolved in CC14 and stocked at −20° C. Before using, it was diluted with deionized water.

3. Adenosine (ADP) and sodium arachidonate (AA) were dissolved in deionized water for use.

(B) Preparation of thrombocytes

A suspension of thrombocytes was prepared according to the reported method. 100 mM of EDTA and the blood from rabbit's ear was mixed in the ratio of 1:4, and immediately separated by centrifuge (120×g) at room temperature for 10 minutes. The thrombocytes enriched upper layer plasma was subjected to centrifuge (500×g) for 10 minutes. After the plasma was removed, the thrombocytes in lower layer were suspended in the Tyrode solution containing EDTA (2 mM) and bovine serum protein (3.5 mg/ml), and subjected to centrifuge (500×g) again for 10 minutes. The thrombocytes obtained was suspended in a Tyrode solution containing no EDTA, and was adjusted to about 4.5×10 cell/ml by a counter. 1 mM of calcium ion (Ca2+) was added to the suspension. 30 minutes after the addition, the experiment was conducted. The composition of Tyrode: bovine serum protein, NaCl (136.9), KCl (2.7), Na3PO3 (0.4), NaHCO3 (11.9), glucose (11.1).

(C) Thrombocyte aggregation and ATP release reaction test

The method reported by Born and Cross (1963) was used to determine the thrombocyte aggregation, in which a Lumi aggregation meter (Model 1020, Payton, Canada) was used. 0.4 ml throbocyte suspension was added into a little glass tube coated with silicone, and stirred at 900 rpm with a small magnetic stirrer. Unless otherwise specified, the antagonist was added 1 minute before the inducing agent, and all the reactions were carried out at 37° C., the degree of aggregation were calculated by following formula:

aggregation (%) = (light absorption before adding inducing agent − light absorption after adding inducing agent) / (light absorption before adding inducing agent − light absorption of Tyrode solution) x 100%

In some experiments, 25 μl of luciferase-luciferin mixture was added, and using the fluorescence resulting from the reaction with ATP to determine the strength of the thrombocyte release reaction on relative basis.

III. Test result

TABLE 1

Rat-PCT Test Results of N-alkyl-2,3,4-trimethylfuro [2,3-c]pyrazole-5-carboxamides

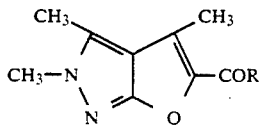

| Compound | R | Dose (mg/Kg) p.o. | Rat No. | Inhibition (%) | score |
|---|---|---|---|---|---|
| control | | 80 | 3 | 0 | 0 |
| | NHCH2CH3 | 80 | 3 | 49.0 | 5 |
| | NHCH2CH2CH(CH3)2 | 80 | 3 | 29.6 | 3 |

TABLE 1-continued

Rat-PCT Test Results of N-alkyl-2,3,4-trimethylfuro [2,3-c]pyrazole-5-carboxamides

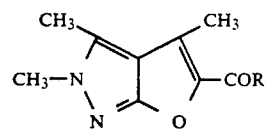

| Compound | R | Dose (mg/Kg) p.o. | Rat No. | Inhibition (%) | score |
|---|---|---|---|---|---|
| | N(CH3)2 | 80 | 3 | 20.2 | 3 |
| | NH(CH2)2CH3 | 80 | 4 | 31.0 | 4 |
| | NH(CH2)3CH3 | 80 | 4 | 31.3 | 4 |
| Theophyllin | | 80 | 4 | 67.8 | 6 |

TABLE 2

Rat-PCT Test Results of N-alkyl-2-ethyl-3,4-dimethylfuro[2,3-c]pyrazole-5-carboxamides

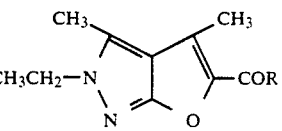

| Compound | R | Dose (mg/Kg) p.o. | Rat No. | Inhibition (%) | score |
|---|---|---|---|---|---|
| control | | 80 | 4 | 0 | 0 |
| | NHCH3 | 80 | 4 | 51.6 | 6 |
| | NHCH2CH3 | 80 | 3 | 19.9 | 2 |
| | NH(CH2)2CH3 | 80 | 3 | 23.1 | 3 |
| | NH(CH2)3CH3 | 80 | 4 | 32.4 | 4 |
| | NHCH(CH3)2 | 80 | 3 | 26.2 | 3 |
| | N(C2H5)2 | 80 | 4 | 30.1 | 4 |
| | NH(CH2)2CH(C6H5)2 | 80 | 4 | 21.2 | 3 |
| | CH=CHCOOH | 80 | 4 | 31.6 | 4 |

TABLE 3

Rat-PCA Test Results of 2-alkyl-3,4-dimethylfuro[2,3-c]pyrazole-5-carboxamides

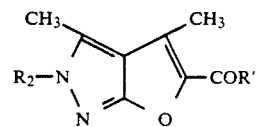

| Compound | R2 | R' | Dose (mg/Kg) p.o. | Rat No. | Inhibition (%) | score |
|---|---|---|---|---|---|---|
| control | | | 80 | 4 | 0 | 0 |
| | —CH(CH3)2 | —NH2 | 80 | 3 | 36.5 | 4 |
| | —CH(CH3)2 | —NHCH3 | 80 | 4 | 53.5 | 6 |
| | —CH(CH3)2 | —NHC2H5 | 80 | 4 | 30.5 | 4 |

TABLE 4

Rat-PCA Test Results of 5-(2,3-dihydro-2-oxo-1,3,4-oxadiazol-5-yl)-2-alkyl-3,4-dimethylfuro[2,3-c]pyrazole

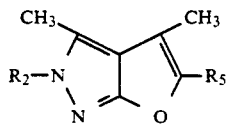

| Compound | $R_2$ | $R'$ | Dose (mg/Kg) p.o. | Rat No. | Inhibition (%) | score |
|---|---|---|---|---|---|---|
| control | | | 80 | 4 | 0 | 0 |
| | $-CH_3$ | $-H$ | 80 | 3 | 53.0 | 6 |
| | $-CH_2CH_3$ | $-H$ | 80 | 4 | 14.1 | 2 |
| | $-CH(CH_3)_2$ | $-H$ | 80 | 4 | 46.1 | 5 |
| | $-CH_2-C_6H_5$ | $-H$ | 80 | 4 | $-27.3$ | 1 |

TABLE 5

Thrombocyte aggregation inhibiting activity of furo[2,3-c]pyrazoles

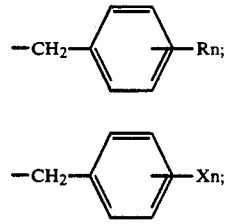

| | | | | Aggregation | | |
|---|---|---|---|---|---|---|
| $R_5$ | $R_2$ | Dose µg/ml | ADP (20 µM) | AA (100 µM) | Collagen (10 µg/ml) | PAF 2 ng/ml |
| control | | | 83.0 + 2.5 | 88.6 + 1.1 | 87.6 + 3.0 | 90.0 + 2.0 |
| $-COOH$ | $-CH_2$-thienyl | 100 | 67.2 + 9.0 | 0.0 + 0.0 | 63.8 + 1.1 | 84.1 + 2.4 |
| $-COOH$ | $-CH_2$-phenyl | 100 | 66.6 + 2.7 | 6.4 + 3.8 | 46.7 + 8.8 | 80.4 + 1.3 |
| $-COOH$ | $-CH_2$-C$_6$H$_4$-Cl | 100 | 51.1 + 4.5 | 21.4 + 1.5 | 2.0 + 1.4 | 75.7 + 4.7 |
| oxadiazolone | $-CH_2CH_3$ | 100 | 40.2 + 11.9 | 8.9 + 7.3 | 80.9 + 5.6 | 87.3 + 2.6 |
| oxadiazolone | $-CH(CH_3)_2$ | 100 | 27.0 + 11.0 | 1.3 + 1.0 | 63.3 + 10.5 | 90.0 + 1.3 |
| oxadiazolone | $-CH_2-C_6H_5$ | 100 | 64.2 + 3.1 | 0.0 + 0.0 | 77.0 + 6.9 | 86.6 + 3.6 |

What is claimed is:

1. A furo[2,3-c]pyrazole compound having the formula (B)

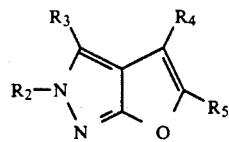

(B)

wherein $R_2$ represents $C_{1-11}$ alkyl; hydroxy $C_{1-4}$ alkyl;

$-CH_2-C_6H_4-R_n$;

$-CH_2-C_6H_4-X_n$;

-continued

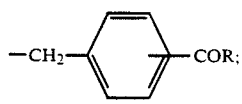

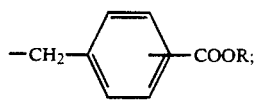

wherein Ar represents 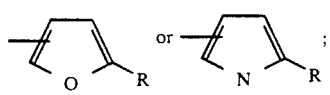

R is hydrogen or $C_{1-6}$ alkyl; n=1 or 2, and X is halogen;
$R_3$ represents $C_{1-9}$ alkyl;
$R_4$ represents $C_{1-9}$ alkyl;
$R_5$ represents hydrogen; —COR; —CH$_2$OH; —CH$_2$OCOR$_1$;
—COX;
—COOR;
—CONHR$_a$;
—CONR$_1$R$_1$;

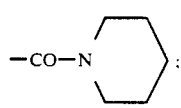

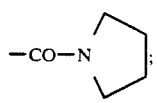

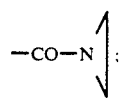

—CONHAr$_1$;

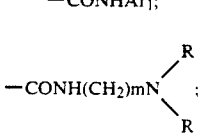

-continued

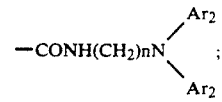

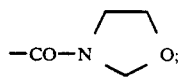

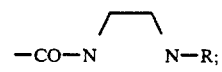

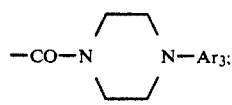

—CONH(CH$_2$)nAr$_3$n;
—CH=CHCONHR;
—CH=CH—COOR;
—CH=C(COOR)$_2$;
—CONHNHCOOR; or

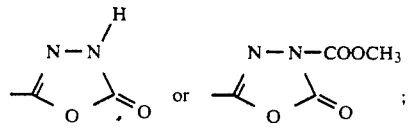

wherein Ar$_1$ is 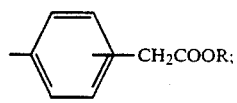

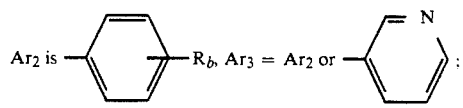

m=1-3; $R_1$ is $C_{1-6}$ alkyl, $R_a$ is R or $C_{3-6}$ cycloalkyl; $R_b$ is hydrogen, halogen or —OCH$_3$; and
R, n and X have the same meanings as defined above; or pharmaceutically acceptable salts thereof.

2. A pharmaceutical composition for inhibiting thrombocyte aggregation, which comprises a therapeutically effective amount of a compound (B) as defined in claim 1 or a pharmaceutically acceptable salt thereof, as an active ingredient, in combination with a pharmaceutically acceptable carrier or diluent for the active ingredient.

3. An antiallergic composition, which comprises a therapeutically effective amount of a compound (B) as defined in claim 1 or a pharmaceutically acceptable salt thereof, as an active ingredient, in combination with a pharmaceutically acceptable carrier or diluent for the active ingredient.

* * * * *